United States Patent [19]

Krüger et al.

[11] Patent Number: 5,739,389

[45] Date of Patent: Apr. 14, 1998

[54] ARYL CARBOXYLIC ACID DERIVATIVES

[75] Inventors: Bernd-Wieland Krüger, Bergisch-Glabach; Reiner Fischer, Monheim; Heinz-Jurgen Bertram, Holzminden; Thomas Bretschneider, Siegburg; Stefan Böhm, Leverkusen; Andreas Krebs, Odenthal-Holz; Thomas Schenke, Bergisch Gladbach; Hans-Joachim Santel, Leverkusen; Klaus Lurssen; Robert R. Schmidt, both of Bergisch; Christoph Erdelen, Leichlingen; Ulrike Wachendorff-Neumann, Monheim; Wilhelm Stendel, Wuppertal, all of Germany

[73] Assignee: Bayer Aktiengesellschaft, Leverkusen, Germany

[21] Appl. No.: 774,469

[22] Filed: Dec. 30, 1996

Related U.S. Application Data

[62] Division of Ser. No. 476,171, Jun. 7, 1995, Pat. No. 5,661,110, which is a division of Ser. No. 233,911, Apr. 28, 1994, Pat. No. 5,474,974, which is a division of Ser. No. 999,058, Dec. 31, 1992, Pat. No. 5,358,924, which is a continuation-in-part of Ser. No. 849,863, Mar. 12, 1992, abandoned.

[30] Foreign Application Priority Data

Mar. 21, 1991 [DE] Germany .................. 41 09 208.2

[51] Int. Cl.$^6$ .................. C07C 55/28; C07C 45/87
[52] U.S. Cl. .................. 562/489; 568/301
[58] Field of Search .................. 548/356.1; 562/489; 568/301

[56] References Cited

U.S. PATENT DOCUMENTS 3,149,115 9/1964 Brabander et al. .................. 260/268
5,494,890 2/1996 Cederbaum et al. .................. 504/281

FOREIGN PATENT DOCUMENTS 9216510 10/1992 WIPO.

OTHER PUBLICATIONS

Journal of the Chemical Society, Chemical Communications, No. 11, 1987, pp. 840–842.
Monatshefte Fur Chemie, vol. 119, No. 6/7, Jun./Jul. 1988 pp. 727–737.
Chemical Abstracts, vol. 73, No. 3, 20 Jul. 1970, p. 290.
Journal of Heterocycleic Chemistry, vol. 25, No. 5, Sep.–Oct. 1988, pp. 1301–1305.
Journal of Heterocyclic Chemistry, vol. 25, No. 5, Sep.–Oct. 1988, pp. 1307–1310.
The Journal of Organic Chemistry, vol. 53, No. 13, 24 Jun. 1988, pp. 2889–2898.
Synthesis, No. 2, 1 Feb. 1990, pp. 167–170.
Lora–Tamayo, Chem Abstracts, vol. 84 (1976) No. 17235n.

*Primary Examiner*—Johann Richter
*Assistant Examiner*—Ebenezer Sackey
*Attorney, Agent, or Firm*—Sprung Kramer Schaefer & Briscoe

[57] ABSTRACT

There are provided an aryl carboxylic acid derivatives of the formula (XVIa)

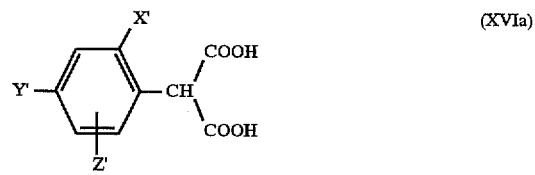

Aryl carboxylic acid derivatives of the formula (XVIa) have a particularly pronounced activity against animal pests, in particular against insects and arachnids, and against weeds.

4 Claims, No Drawings

ARYL CARBOXYLIC ACID DERIVATIVES

This application is a divisional of application Ser. No. 08/476,171, filed Jun. 7, 1995, U.S. Pat. No. 5,666,110 which is a division of application Ser. No. 08/233,911, filed Apr. 28, 1994, now U.S. Pat. No. 5,474,974, which is a division of Ser. No. 07/999,058, filed Dec. 31, 1992, now U.S. Pat. No. 5,358,924, which is a c-i-p of Ser. No. 07/849,863, filed Mar. 12, 1992, now abandoned.

The invention relates to new polycyclic 3-hydroxy-4-aryl-5-oxo-pyrazoline derivatives, to a plurality of processes for their preparation, and to their use as insecticides, acaricides and herbicides.

Certain 3H-pyrazol-3-one derivatives such as, for example, 1,2-diethyl-1,2-dihydro-5-hydroxy-4-phenyl-3H-pyrazol-3-one or {[5-oxo-1,2-diphenyl-4-(p-sulphophenyl)-3-pyrazolin-3-yl]-oxy}-disodium salt or p-(3-hydroxy-5-oxo-1,2-diphenyl-3-pyrazolin-4-yl)-benzenesulphonic acid are known from the literature (cf. J. Heterocycl. Chem., 25 (5), 1301–1305, 1988 or J. Heterocycl. Chem., 25 (5), 1307–1310, 1988 or Zh. Obshch. Khim., 34 (7), 2397–2402, 1964). However, a biological action of these compounds is not described.

Furthermore, it is known that the trisodium salt of 4,4',4''-(5-hydroxy-3-oxo-1H-pyrazole-1,2,4(3H)-triyl)tris-benzenesulphonic acid has pharmacological properties (cf. Farmakol. Toksikol. (Moscow), 39 (2), 180–186, 1976). However, its use in plant protection is not known.

There have now been new 3-hydroxy-4-aryl-5-oxo-pyrazoline derivatives of the formula (I)

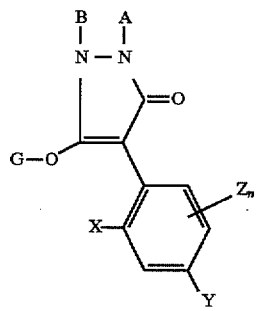

in which

A and B are identical or different and independently of one another in each case represent hydrogen, alkyl, alkenyl, alkynyl, alkoxyalkyl, alkylthioalkyl, cycloalkyl or optionally substituted aryl or A and B together represent the bivalent radical of a saturated or unsaturated, optionally substituted, mono-, bi-, tri- or polycyclic system, X represents alkyl, halogen or alkoxy, Y represents hydrogen, alkyl, halogen, alkoxy or halogenoalkyl, Z represents alkyl, halogen or alkoxy, n represents a number 0, 1, 2 or 3, G represents hydrogen (a) or the groups $-CO-R^1$, (b)

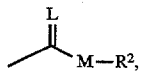

$-SO_2-R^3$, (d)

-continued

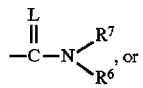

E (g)

in which

E represents a metal ion equivalent or an ammonium ion,

L and M represents oxygen and/or sulphur, $R^1$ represents optionally halogen-substituted alkyl, alkenyl, alkoxyalkyl, alkylthioalkyl, polyalkoxyalkyl or cycloalkyl which can be interrupted by hetero atoms, optionally substituted phenyl, optionally substituted phenylalkyl, substituted hetaryl, substituted phenoxyalkyl or substituted hetaryloxyalkyl and $R^2$ represents optionally halogen-substituted alkyl, alkenyl, alkoxyalkyl, polyalkoxyalkyl or optionally substituted phenyl or benzyl, $R^3$, $R^4$ and $R^5$ independently of one another represent optionally halogen-substituted alkyl, alkoxy, alkylamino, dialkylamino, alkylthio, alkenylthio, alkynylthio or cycloalkylthio, and optionally substituted phenyl, phenoxy or phenylthio, $R^6$ and $R^7$ independently of one another represent hydrogen, optionally halogen-substituted alkyl, alkenyl, alkoxy or alkoxyalkyl, optionally substituted phenyl, optionally substituted benzyl, or $R^6$ and $R^7$ together represent an alkylene radical which is optionally interrupted by oxygen.

Taking into account various meanings (a), (b), (c), (d), (e), (f) and (g) of group G of the general formula (I), the following main structures (Ia) to (Ig) result:

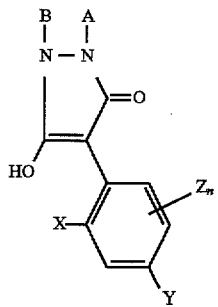

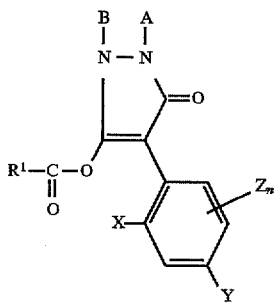

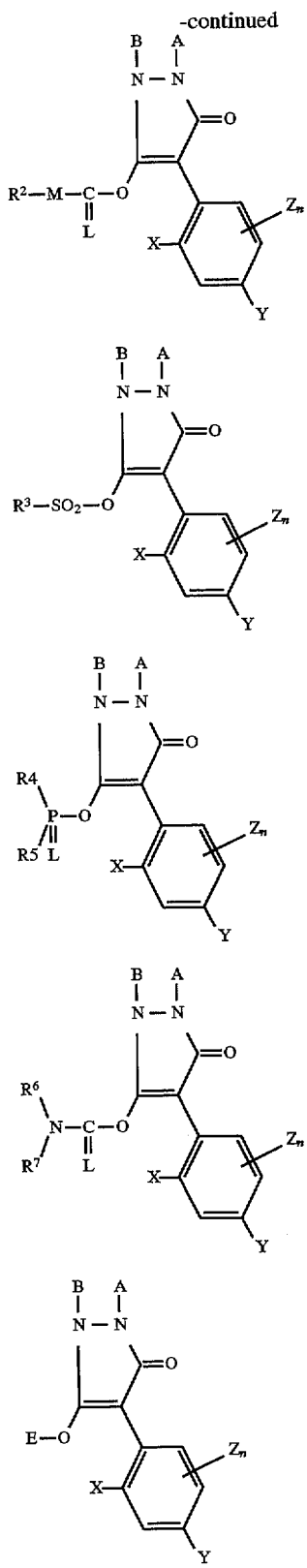

mixture of stereoisomers. They can be used in the form of their mixtures of diastereoisomers or in the form of pure diastereomers or enantiomers.

Furthermore, it has been found that the new 3-hydroxy-4-aryl-5-oxo-pyrazoline derivatives of the formula (I) are obtained by one of the processes described below.

(A) 3-Hydroxy-4-aryl-5-oxo-pyrazolines of the formula

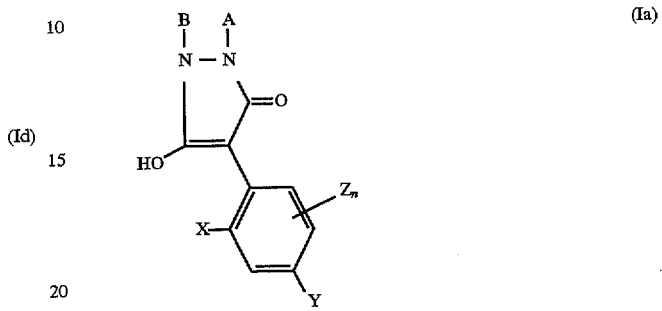

in which

A, B, X, Y, Z and n have the abovementioned meanings, are obtained when (α) halogenocarbonyl ketenes of the formula (II)

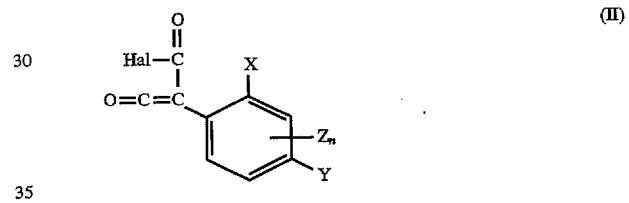

in which

X, Y, Z and n have the abovementioned meaning and

Hal represents halogen, in particular chlorine or bromine, or (β) malonic acid derivatives of the formula (III)

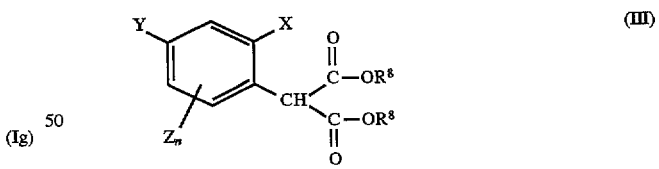

in which

X, Y, Z and n have the abovementioned meaning and $R^8$ represents alkyl, are reacted with hydrazines of the formula (IV)

in which

A and B have the abovementioned meaning, if appropriate in the presence of a diluent and if appropriate in the presence of a base;

or where

A, B, E, L, M, X, Y, $Z_n$, $R^1$, $R^2$, $R^3$, $R^4$, $R^5$, $R^6$ and $R^7$ have the abovementioned meanings.

Due to one or more centres of chirality, the compounds of the formula (Ia)–(Ig) are generally obtained in the form of a (B) compounds of the formula (Ib)

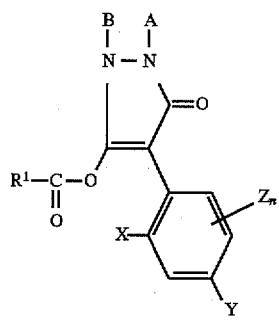
(Ib)

in which

A, B, X, Y, Z, $R^1$ and n have the abovementioned meaning, are obtained when compounds of the formula (Ia)

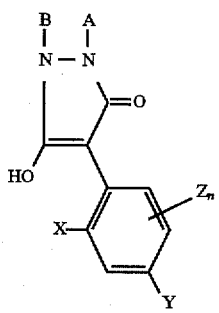
(Ia)

in which

A, B, X, Y, Z and n have the abovementioned meaning,

α) are reacted with acid halides of the general formula (V)

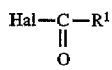
(V)

in which $R^1$ has the abovementioned meaning and

Hal represents halogen, in particular chlorine and bromine, if appropriate in the presence of a diluent and if appropriate in the presence of an acid-binding agent, or β) are reacted with carboxylic anhydrides of the general formula (VI)

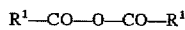
(IV)

in which $R^1$ has the abovementioned meaning, if appropriate in the presence of a diluent and if appropriate in the presence of an acid-binding agent;

or (C) compounds of the formula (Ic-1)

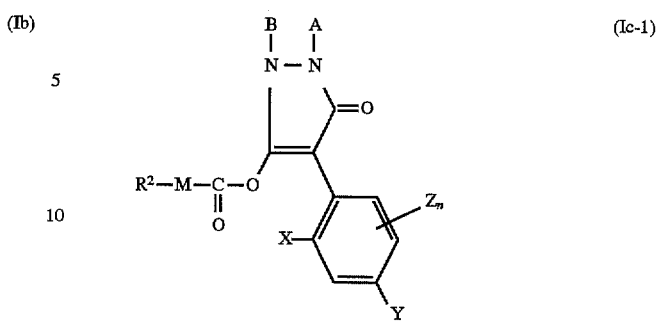
(Ic-1)

in which

A, B, X, Y, Z, $R^2$ and n have the abovementioned meaning and

M represents oxygen or sulphur, are obtained when compounds of the formula (Ia)

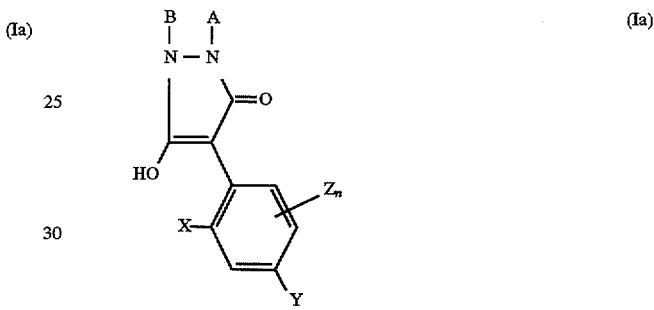
(Ia)

in which

A, B, X, Y, Z and n have the abovementioned meaning, are reacted with chloroformic ester or chloroformic thioester of the general formula (VII)

$R^2$—M—CO—Cl (VII)

in which $R^2$ and M have the abovementioned meaning, if appropriate in the presence of a diluent and if appropriate in the presence of an acid-binding agent;

or (D) compounds of the formula (Ic-2)

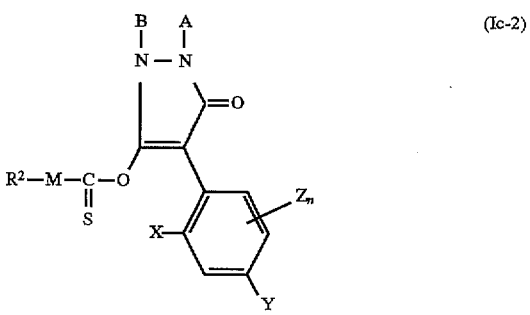
(Ic-2)

in which

A, B, $R^2$, X, Y, Z and n have the abovementioned meaning, and

M represents oxygen or sulphur, are obtained when compounds of the formula (Ia)

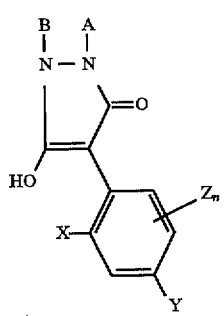
(Ia)

in which

A, B, X, Y, Z and n have the abovementioned meaning,

α) are reacted with chloromonothioformic esters or chlorodithioformic esters of the general formula (VIII)

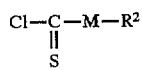
(VIII)

in which

M and $R^2$ have the abovementioned meaning, if appropriate in the presence of a diluent and if appropriate in the presence of an acid-binding agent, or β) are reacted with carbon disulphide and subsequently with alkyl halides of the general formula (IX)

(IX)

in which $R^2$ has the abovementioned meaning and

Hal represents chlorine, bromine or iodine or (E) compounds of the formula (Id)

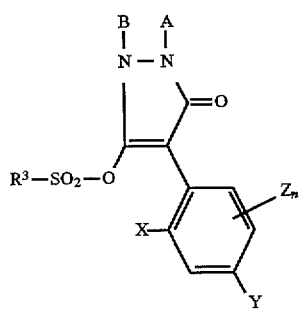
(Id)

in which

A, B, X, Y, Z, $R^3$ and n have the abovementioned meaning, are obtained when compounds of the formula (Ia)

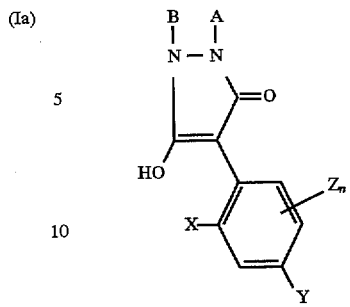
(Ia)

in which

A, B, X, Y, Z and n have the abovementioned meaning, are reacted with sulphonyl chlorides of the general formula (X)

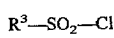
(X)

in which $R^3$ has the abovementioned meaning, if appropriate in the presence of a diluent and if appropriate in the presence of an acid-binding agent;

or (F) the compounds of the formula (Ie)

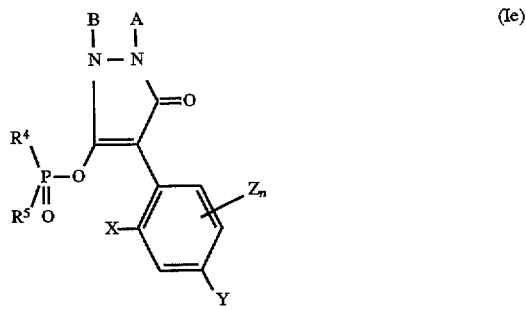
(Ie)

in which

A, B, L, X, Y, Z, $R^4$, $R^5$ and n have the abovementioned meaning are obtained when
3-hydroxy-4-aryl-5-oxo-pyrazolines of the formula (Ia)

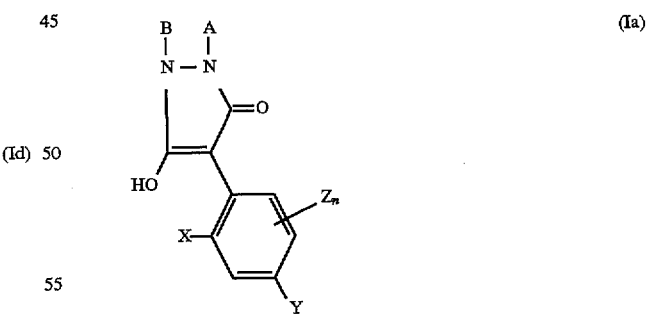
(Ia)

in which

A, B, X, Y, Z and n have the abovementioned meaning, are reacted with phosphorus compounds of the general formula (XI)

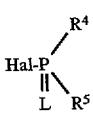
(XI)

in which

L, $R^4$ and $R^5$ have the abovementioned meaning and

Hal represents halogen, in particular chlorine and bromine, if appropriate in the presence of a diluent and if appropriate in the presence of an acid-binding agent;

or (G) compounds of the formula (If)

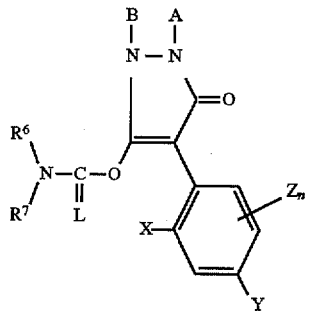

(If)

in which

A, B, L, X, Y, Z, $R^6$, $R^7$ and n have the abovementioned meaning are obtained when compounds of the formula (Ia)

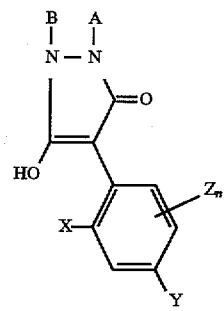

(Ia)

in which

A, B, X, Y, Z and n have the abovementioned meaning,

α) are reacted with isocyanates of the general formula (XII)

$R^6$—N=C=O  (XII)

in which $R^6$ has the abovementioned meaning, if appropriate in the presence of a diluent and if appropriate in the presence of a catalyst, or β) are reacted with carbamoyl chlorides or thiocarbamoyl chlorides of the general formula (XIII)

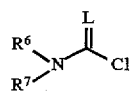

(XIII)

in which

L, $R^6$ and $R^7$ have the abovementioned meaning, if appropriate in the presence of a diluent and if appropriate in the presence of an acid-binding agent, or (H) compounds of the formula (Ig)

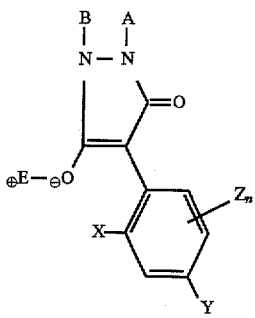

(Ig)

in which

A, B, X, Y, Z and n have the abovementioned meaning, and

E represents a metal ion equivalent or an ammonium ion, are obtained when compounds of the formula (Ia)

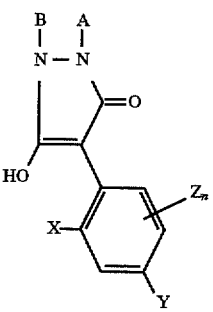

(Ia)

in which

A, B, X, Y, Z and n have the abovementioned meaning, are reacted with metal hydroxides or amines of the general formulae (XIV) and (XV)

$Me_sOH_t$  (XIV)

$R^5$—N—$R^7$ (XV)

in which

Me represents monovalent or divalent metal ions, s and t represent the number 1 and 2 and $R^5$, $R^6$ and $R^7$ independently of one another represent hydrogen and alkyl, if appropriate in the presence of a diluent.

Furthermore, it has been found that the new 3-hydroxy-4-aryl-5-oxo-pyrazoline derivatives of the formula (I) are distinguished by outstanding insecticidal, acaricidal and herbicidal actions.

Preferred 3-hydroxy-4-aryl-5-oxo-pyrazoline derivatives of the formula (I) are those in which A and B are identical or different and independently of one another in each case represent hydrogen, $C_1$-$C_8$-alkyl, $C_2$-$C_8$-alkenyl, $C_2$-$C_8$-alkynyl, $C_1$-$C_8$-alkoxy-$C_1$-$C_8$-alkyl, $C_1$-$C_8$-alkylthio-$C_1$-$C_8$-alkyl, cycloalkyl having 3 to 7 carbon atoms, or represent phenyl which is optionally monosubstituted or polysubstituted by identical or different substituents, suitable phenyl substituents being the phenyl substituents mentioned in the case of $R^3$, $R^4$ and $R^5$, or A and B together represent the bivalent radical of a saturated or unsaturated mono-, di-, tri- or polycyclic system which is optionally monosubstituted or polysubstituted by identical or different substituents, suitable substituents being: halogen, optionally halogen-substituted $C_1$–$C_{20}$-alkyl, $C_2$–$C_{20}$-alkenyl, $C_1$–$C_8$-alkyloxy-$C_2$–$C_8$-alkyl, $C_1$–$C_8$-polyalkoxy-$C_2$–$C_8$-alkyl, or phenyl or benzyl which are optionally substituted by halogen, nitro, $C_1$–$C_6$-alkyl, $C_1$–$C_6$-alkoxy or $C_1$–$C_6$-halogenoalkyl, X represents $C_1$–$C_6$-alkyl, halogen or $C_1$–$C_6$-alkoxy, Y represents hydrogen, $C_1$–$C_6$-alkyl, halogen, $C_1$–$C_6$-alkoxy or $C_1$–$C_3$-halogenoalkyl, Z represents $C_1$–$C_6$-alkyl, halogen or $C_1$–$C_6$-alkoxy, n represents a number 0, 1, 2 or 3, G represents hydrogen (a) or the groups $-CO-R^1$, (b)

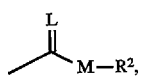 (c)

$-SO_2-R^3$, (d)

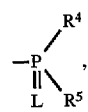 (e)

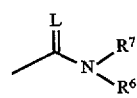 (f)

or E (g)

in which

E represents a metal ion equivalent or an ammonium ion,

L and M represents oxygen and/or sulphur, $R^1$ represents optionally halogen-substituted $C_1$–$C_{20}$-alkyl, $C_2$–$C_{20}$-alkenyl, $C_1$–$C_8$-alkoxy-$C_2$–$C_8$-alkyl, $C_1$–$C_8$-alkylthio-$C_2$–$C_8$-alkyl, $C_1$–$C_8$-polyalkoxy-$C_2$–$C_8$-alkyl or cycloalkyl which has 3 to 8 ring atoms and which can be interrupted by oxygen and/or sulphur atoms, or represents phenyl which is optionally substituted by halogen, nitro, $C_1$–$C_6$-alkyl, $C_1$–$C_6$-alkoxy, $C_1$–$C_6$-halogenoalkyl or $C_1$–$C_6$-halogenoalkoxy-, or represents phenyl-$C_1$–$C_6$-alkyl which is optionally substituted by halogen, $C_1$–$C_6$-alkyl, $C_1$–$C_6$-alkoxy, $C_1$–$C_6$-halogenoalkyl or $C_1$–$C_6$-halogenoalkoxy-, or represents hetaryl which is optionally substituted by halogen and/or $C_1$–$C_6$-alkyl, or represents phenoxy-$C_1$–$C_6$-alkyl which is optionally substituted by halogen and $C_1$–$C_6$-alkyl-, or represents hetaryloxy-$C_1$–$C_6$-alkyl which is optionally substituted by halogen, amino and $C_1$–$C_6$-alkyl-, $R^2$ represents optionally halogen-substituted $C_1$–$C_{20}$-alkyl, $C_2$–$C_{20}$-alkenyl, $C_1$–$C_8$-alkoxy-$C_2$–$C_8$-alkyl or $C_1$–$C_8$-polyalkoxy-$C_2$–$C_8$-alkyl, or represents phenyl or benzyl which are optionally substituted by halogen, nitro, $C_1$–$C_5$-alkyl, $C_1$–$C_6$-alkoxy or $C_1$–$C_6$-halogenoalkyl-, $R^3$, $R^4$ and $R^5$ independently of one another represent optionally halogen-substituted $C_1$–$C_8$-alkyl, $C_1$–$C_8$-alkoxy, $C_1$–$C_8$-alkylamino, di-($C_1$–$C_8$)-alkylamino, $C_1$–$C_8$-alkylthio, $C_2$–$C_5$-alkenylthio, $C_2$–$C_5$-alkynylthio or $C_3$–$C_7$-cycloalkylthio, or represent phenyl, phenoxy or phenylthio which are optionally substituted by halogen, nitro, cyano, $C_1$–$C_4$-alkoxy, $C_1$–$C_4$-halogenoalkoxy, $C_1$–$C_4$-alkylthio, $C_1$–$C_4$-halogenoalkylthio, $C_1$–$C_4$-alkyl or $C_1$–$C_4$-halogenoalkyl, $R^6$ and $R^7$ independently of one another represent hydrogen, optionally halogen-substituted $C_1$–$C_{20}$-alkyl, $C_1$–$C_{20}$-alkoxy, $C_2$–$C_8$-alkenyl or $C_1$–$C_{20}$-alkoxy-$C_1$–$C_{20}$-alkyl, or phenyl which is optionally substituted by halogen, $C_1$–$C_{20}$-halogenoalkyl, $C_1$–$C_{20}$-alkyl or $C_1$–$C_{20}$-alkoxy, or benzyl which is optionally substituted by halogen, $C_1$–$C_{20}$-alkyl, $C_1$–$C_{20}$-halogenoalkyl or $C_1$–$C_{20}$-alkoxy, or together represent a $C_2$–$C_6$-alkylene ring which is optionally interrupted by oxygen.

Due to one or more centres of chirality, the compounds of the formula (Ia)–(Ig) are generally obtained in the form of stereoisomer mixtures. They can be used in the form of their diastereomer mixtures as well as in the form of pure diastereomers or enantiomers.

Particularly preferred compounds of the formula (I) are those in which

A and B are identical or different and independently of one another in each case represent hydrogen, $C_1$–$C_6$-alkyl, $C_2$–$C_6$-alkenyl, $C_2$–$C_6$-alkynyl, —$C_1$–$C_6$-alkoxy-$C_1$–$C_6$-alkyl, $C_1$–$C_6$-alkylthio-$C_1$–$C_6$-alkyl or cycloalkyl having 3 to 7 carbon atoms, or represent phenyl which is optionally monosubstituted to trisubstituted by identical or different substituents, suitable phenyl substituents being the phenyl substituents mentioned in the case of $R^3$, $R^4$ and $R^5$, or A and B together with the two nitrogen atoms of the pyrazoline ring represent a group of the formulae 1 to 16 listed below

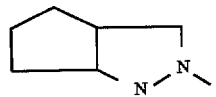 1

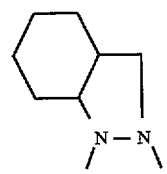 2

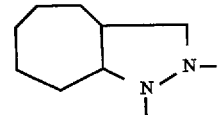 3

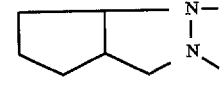 4

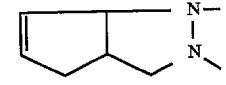 5

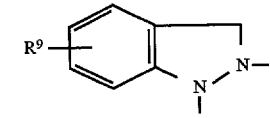 6

-continued

7
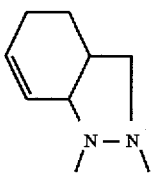

8
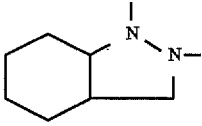

9
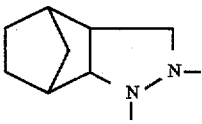

10
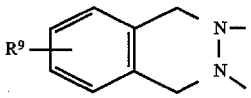

11
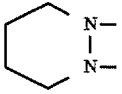

12
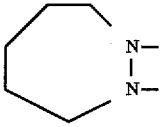

13
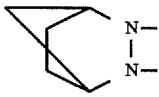

14
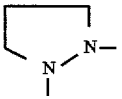

15
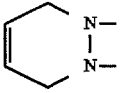

16
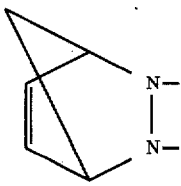

which is optionally monosubstituted or polysubstituted by identical or different substituents, suitable substituents being halogen, optionally halogen-substituted $C_1$–$C_{16}$-alkyl, $C_2$–$C_{16}$-alkenyl, $C_1$–$C_{16}$-alkoxy-$C_2$–$C_6$-alkyl or $C_1$–$C_6$-polyalkoxy-$C_2$–$C_6$-alkyl, or phenyl or benzyl which are optionally substituted by halogen, nitro, $C_1$–$C_4$-alkyl, $C_1$–$C_3$-alkoxy or $C_1$–$C_3$-halogenoalkyl, and $R^9$ represents halogen or optionally halogen-substituted $C_1$–$C_2$-alkyl or $C_1$–$C_2$-alkoxy, X represents $C_1$–$C_4$-alkyl, halogen or $C_1$–$C_4$-alkoxy, Y represents hydrogen, $C_1$–$C_4$-alkyl, halogen, $C_1$–$C_4$-alkoxy or $C_1$–$C_2$-halogenoalkyl, Z represents $C_1$–$C_4$-alkyl, halogen or $C_1$–$C_4$-alkoxy, n represents a number 0, 1, 2 or 3, G represents hydrogen (a) or the groups $-CO-R^1$, (b)

(c)
$$\overset{L}{\underset{M-R^2}{\|}}$$

$-SO_2-R^3$, (d)

(e)
$$-\underset{\underset{L}{\|}}{P}\overset{R^4}{\underset{R^5}{\diagdown}}$$

(f)
$$\overset{L}{\underset{N}{\|}}\overset{R^7}{\underset{R^8}{\diagdown}}$$

or

E (g)

in which

E represents a metal ion equivalent or an ammonium ion,

L and M in each case represents oxygen and/or sulphur, $R^1$ represents optionally halogen-substituted $C_1$–$C_{16}$-alkyl, $C_2$–$C_{16}$-alkenyl, $C_1$–$C_6$-alkoxy-$C_2$–$C_6$-alkyl, $C_1$–$C_{16}$-alkylthio-$C_2$–$C_6$-alkyl, $C_1$–$C_6$-polyalkoxy-$C_2$–$C_6$-alkyl or cycloalkyl which has 3 to 7 ring atoms and which can be interrupted by 1–2 oxygen and/or sulphur atoms, or phenyl which is optionally by halogen-, nitro-, $C_1$–$C_4$-alkyl-, $C_1$–$C_4$-alkoxy-, $C_1$–$C_3$-halogenoalkyl- or $C_1$–$C_3$-halogenoalkoxy-substituted phenyl, or represents optionally by halogen-, $C_1$–$C_4$-alkyl-, $C_1$–$C_4$-alkoxy-, $C_1$–$C_3$-halogenoalkyl- or $C_1$–$C_3$-halogenoalkoxy-substituted phenyl-$C_1$–$C_4$-alkyl, or represents optionally by halogen- and/or $C_1$–$C_6$-alkyl-substituted hetaryl, or represents optionally by halogen- and $C_1$–$C_4$-alkyl-substituted phenoxy-$C_1$–$C_5$-alkyl, or represents hetaryloxy-$C_1$–$C_5$-alkyl which is optionally substituted by halogen, amino and $C_1$–$C_4$-alkyl-, $R^2$ represents optionally halogen-substituted $C_1$–$C_{16}$-alkyl, $C_2$–$C_{16}$-alkenyl, $C_1$–$C_{16}$-alkoxy-$C_2$–$C_6$-alkyl or $C_1$–$C_6$-polyalkoxy-$C_2$–$C_6$-alkyl, or represents optionally by halogen-, nitro-, $C_1$–$C_4$-alkyl-, $C_1$–$C_3$-alkoxy- or $C_1$–$C_3$-halogenoalkyl-substituted phenyl or benzyl, $R^3$, $R^4$ and $R^5$ independently of one another represent optionally halogen-substituted $C_1$–$C_6$-alkyl, $C_1$–$C_6$-alkoxy, $C_1$–$C_6$-alkylamino, di-($C_1$–$C_6$)-alkylamino, $C_1$–$C_6$-alkylthio, $C_3$–$C_4$-alkenylthio, $C_2$–$C_4$-alkynylthio or $C_3$–$C_6$-cycloalkylthio, or represent phenyl, phenoxy or phenylthio which are optionally substituted by fluorine, chlorine, bromine, nitro, cyano, $C_1$–$C_3$-alkoxy, $C_1$–$C_3$-halogenoalkoxy, $C_1$–$C_3$-alkylthio, $C_1$–$C_3$-halogenoalkylthio, $C_1$–$C_3$-alkyl or $C_1$–$C_3$-halogeno-alkyl, $R^6$ and $R^7$ independently of one another represents hydrogen, optionally halogen-substituted $C_1$–$C_{20}$-alkyl, $C_1$–$C_{20}$-alkoxy, $C_2$–$C_8$-alkenyl or $C_1$–$C_{20}$-alkoxy-$C_1$–$C_{20}$-alkyl, or represents phenyl which is optionally substituted by halogen, $C_1$–$C_5$-halogenoalkyl, $C_1$–$C_5$-alkyl or $C_1$–$C_5$-alkoxy, or represents benzyl which is optionally substituted by halogen, $C_1$–$C_5$-alkyl, $C_1$–$C_5$-halogenoalkyl or $C_1$–$C_5$-alkoxy.

Very particularly preferred compounds of the formula (I) are those in which

A and B are identical or different and independently of one another in each case represent hydrogen, $C_1$–$C_4$-alkyl, $C_2$–$C_4$-alkenyl, $C_2$–$C_4$-alkynyl, —$C_1$–$C_4$-alkoxy-$C_1$–$C_4$-alkyl, $C_1$–$C_4$-alkylthio-$C_1$–$C_4$-alkyl or cycloalkyl having 3 to 7 carbon atoms, or represent phenyl which is optionally monosubstituted to trisubstituted by identical or different substituents, suitable phenyl substituents being the phenyl substituents mentioned in the case of $R^3$, $R^4$ and $R^5$, or A and B together with the two nitrogen atoms of the pyrazoline ring represent a group of the formulae 1 to 14 listed below

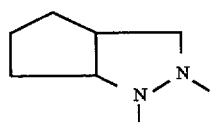
1

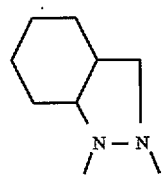
2

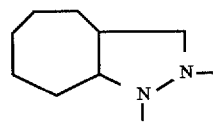
3

4

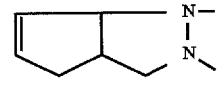
5

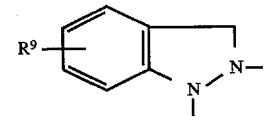
6

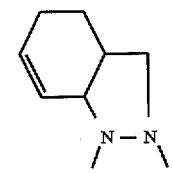
7

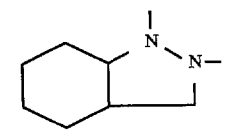
8

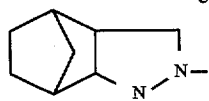
9

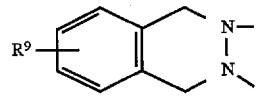
10

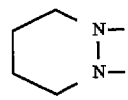
11

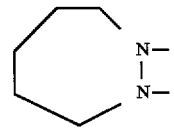
12

13

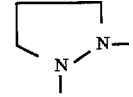
14

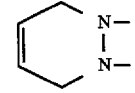
15

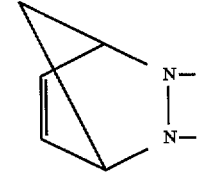
16 which is optionally monosubstituted to trisubstituted by identical or different substituents, suitable substituents being halogen, or $C_1$–$C_{14}$-alkyl, $C_2$–$C_{14}$-alkenyl, $C_1$–$C_4$-alkoxy-$C_2$–$C_6$-alkyl or $C_1$–$C_4$-polyalkoxy-$C_2$–$C_6$-alkyl, which are optionally substituted by fluorine or chlorine, or phenyl or benzyl which are optionally substituted by fluorine, chlorine, nitro, methyl, ethyl, propyl, i-propyl, methoxy, ethoxy, or trifluoromethyl, and $R^9$ represents fluorine, chlorine, or $C_1$–$C_2$-alkyl or $C_1$–$C_2$-alkoxy which are optionally substituted by fluorine and/or chlorine, X represents methyl, ethyl, propyl, i-propyl, fluorine, chlorine, bromine, methoxy and ethoxy Y represents hydrogen, methyl, ethyl, propyl, i-propyl, butyl, i-butyl, tert-butyl, fluorine, chlorine, bromine, methoxy, ethoxy and trifluoromethyl, Z represents methyl, ethyl, i-propyl, butyl, i-butyl, tert-butyl, fluorine, chlorine, bromine, methoxy and ethoxy, n represents a number 0, 1, 2 or 3, G represents hydrogen (a) or the groups $$-CO-R^1, \quad (b)$$

-continued

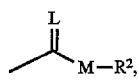
(c)

$-SO_2-R^3$, (d)

(e)

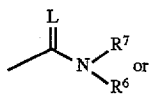
(f)

E (g)

in which

E represents a metal ion equivalent or an ammonium ion,

L and M represents oxygen and/or sulphur, $R^1$ represents optionally fluorine- or chlorine-substituted $C_1-C_{14}$-alkyl, $C_2-C_{14}$-alkenyl, $C_1-C_4$-alkoxy-$C_2-C_6$-alkyl, $C_1-C_4$-alkylthio-$C_2-C_6$-alkyl, $C_1-C_4$-polyalkoxy-$C_2-C_4$-alkyl or cycloalkyl which has 3 to 6 ring atoms and which can be interrupted by 1 to 2 oxygen and/or sulphur atoms, or represents phenyl which is optionally substituted by fluorine, chlorine, bromine, methyl, ethyl, propyl, i-propyl, methoxy, ethoxy, trifluoromethyl, trifluoromethoxy or nitro-, or represents phenyl-$C_1-C_3$-alkyl which is optionally substituted by fluorine, chlorine, bromine, methyl, ethyl, propyl, i-propyl, methoxy, ethoxy, trifluoromethyl or trifluoromethoxy-, or represents pyridyl, pyrimidyl, thiazolyl and pyrazolyl which are optionally substituted by fluorine, chlorine, bromine, methyl or ethyl-, or represents phenoxy-$C_1-C_4$-alkyl which is optionally substituted by fluorine, chlorine, methyl or ethyl-, or represents pyridyloxy-$C_1-C_4$-alkyl, pyrimidyloxy-$C_1-C_4$-alkyl and thiazolyloxy-$C_1-C_4$-alkyl which are optionally substituted by fluorine, chlorine, amino, methyl- or ethyl, $R^2$ represents $C_1-C_{14}$-alkyl, $C_2-C_{14}$-alkenyl, $C_1-C_4$-alkoxy-$C_2-C_6$-alkyl or $C_1-C_4$-polyalkoxy-$C_2-C_6$-alkyl, which are optionally substituted by fluorine or chlorine, or represents phenyl or benzyl which are optionally substituted by fluorine, chlorine, nitro, methyl, ethyl, propyl, i-propyl, methoxy, ethoxy, or trifluoromethyl, $R^3$, $R^4$ and $R^5$ independently of one another represent $C_1-C_4$-alkyl, $C_1-C_4$-alkoxy, $C_1-C_4$-alkylamino, di-($C_1-C_4$)-alkylamino or $C_1-C_4$-alkylthio, which are optionally substituted by fluorine or chlorine, or represent phenyl, phenoxy or phenylthio which are optionally substituted by fluorine, chlorine, bromine, nitro, cyano, $C_1-C_2$-alkoxy, $C_1-C_4$-fluoroalkoxy, $C_1-C_2$-chloroalkoxy, $C_1-C_2$-alkylthio, $C_1-C_2$-fluoroalkylthio, $C_1-C_2$-chloroalkylthio, $C_1-C_3$-alkyl or $C_1-C_3$-halogenoalkyl, $R^6$ and $R^7$ independently of one another represents $C_1-C_{10}$-alkyl, $C_1-C_{10}$-alkoxy or $C_1-C_{10}$-alkoxy-$C_1-C_{10}$-alkyl, which are optionally substituted by fluorine, chlorine or bromine, or represents phenyl which is optionally substituted by fluorine, chlorine, bromine, $C_1-C_{20}$-halogenoalkyl, $C_1-C_{20}$-alkyl or $C_1-C_4$-alkoxy, or represents benzyl which is optionally substituted by fluorine, chlorine, bromine, $C_1-C_4$-alkyl, $C_1-C_4$-halogenoalkyl or $C_1-C_4$-alkoxy.

Especially preferred compounds of the formula (I) are those in which

A and B are identical or different and independently of one another in each case represent hydrogen, $C_1-C_4$-alkyl, $C_2-C_4$-alkenyl, $C_2-C_4$-alkynyl, $C_1-C_4$-alkoxy-$C_1-C_4$-alkyl, $C_1-C_4$-alkylthio-$C_1-C_4$-alkyl or cycloalkyl having 3 to 7 carbon atoms, or phenyl which is optionally monosubstituted to trisubstituted by identical or different substituents, suitable phenyl substituents being the phenyl substituents mentioned in the case of $R^3$, $R^4$ and $R^5$, or A and B together with the two nitrogen atoms of the pyrazoline ring represent a group of the formulae 1', 2', 3' or 4' listed below

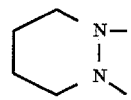
1'

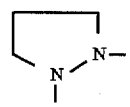
2'

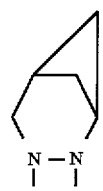
3'

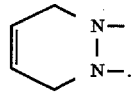
4' which is optionally monosubstituted to trisubstituted by identical or different substituents, suitable substituents being halogen, or optionally fluorine- or chlorine-substituted $C_1-C_8$-alkyl, $C_2-C_8$-alkenyl and $C_1-C_4$-alkoxy-$C_1-C_4$-alkyl, and X, Y, Z, n and G have the abovementioned meaning.

If, for example, (chlorocarbonyl)-2,4,6-trimethylphenyl ketene and 1,2-diazacyclopentane are used as starting compounds according to process (A-α), the course of the process according to the invention can be represented by the following equation:

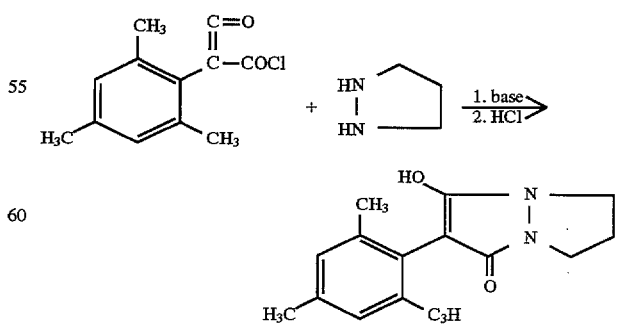

If, for example, diethyl mesitylmalonate and 1,2-diazacyclopentane are used as starting compounds according to process (A-β), the course of the process according to the invention can be represented by the following equation:

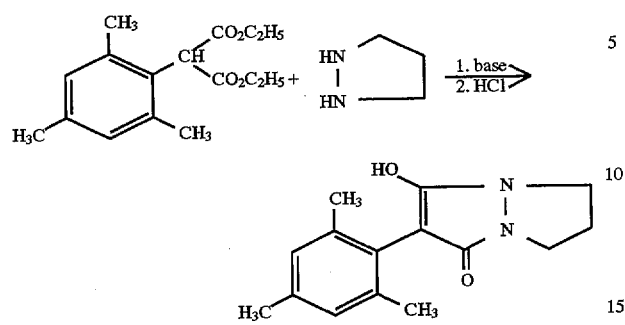

If, for example, 3-(2,4,6-trimethylphenyl)-1,5-diaza-bicyclo-(3,3,0¹·⁵)-octane-2,4-dione and pivaloyl chloride are used starting substances according to process (B-α), the course of the process according to the invention can be represented by the following equation.

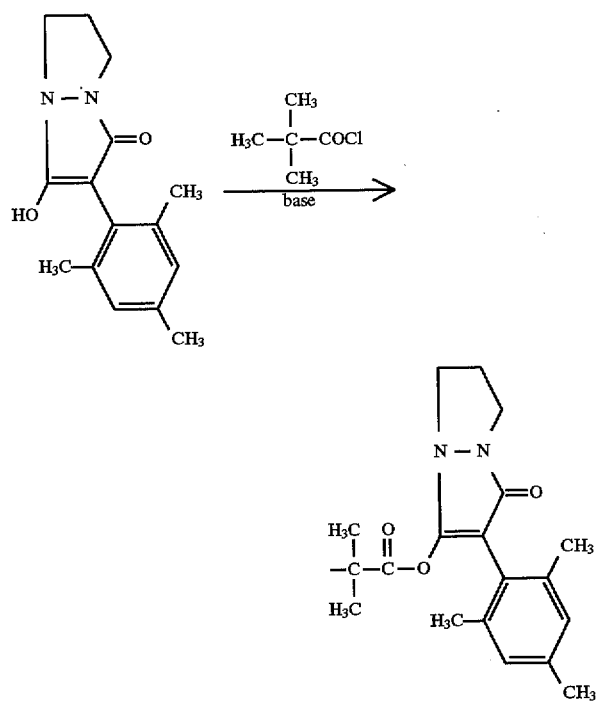

If 8-(2,4,5-trimethylphenyl)-1,6-diaza-bicyclo-(4,3-,0¹·⁶) nonane-7,9-dione and acetic anhydride are used as starting compounds according to process (B-β), the course of the process according to the invention can be represented by the following equation.

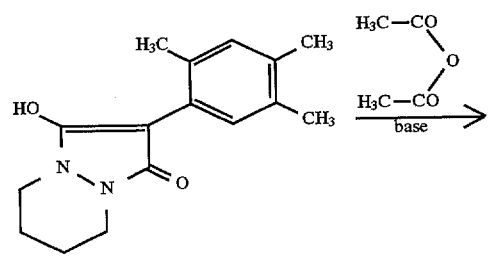

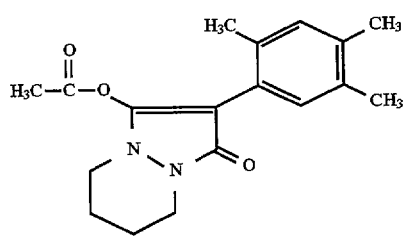

If 8-(2,4-dichlorophenyl)-1,6-diaza-bicyclo-(4,3,0¹·⁶) nonane-7,9-dione and ethoxyethyl chloroformate are used as starting compounds according to process (C), the course of the process according to the invention can be represented by the following equation.

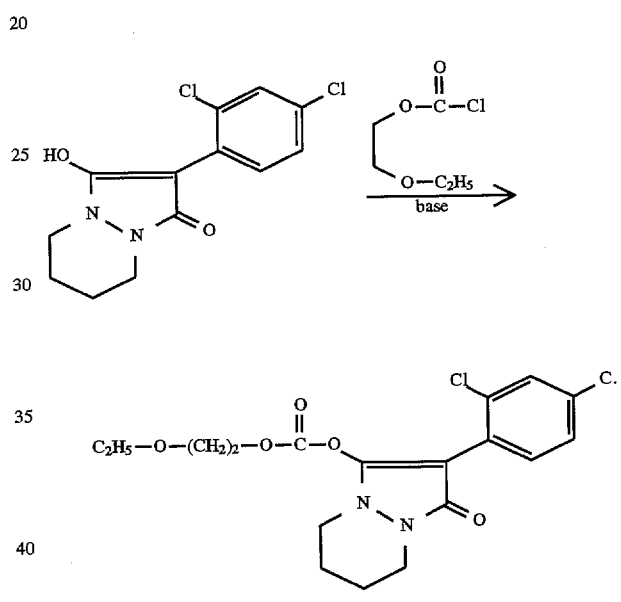

If 3-(2,4,6-trimethylphenyl)-1,5-diaza-bicyclo-(3,3,0¹·⁵) octane-2,4-dione and methyl chloromonothioformate are used as starting materials according to process (D-α), the course of the process according to the invention can be represented as follows:

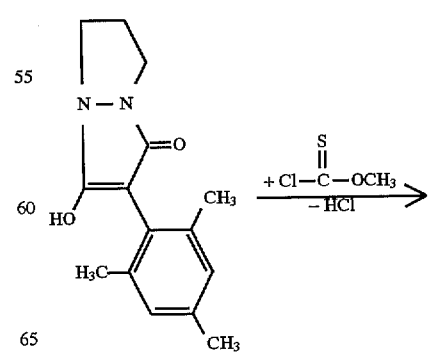

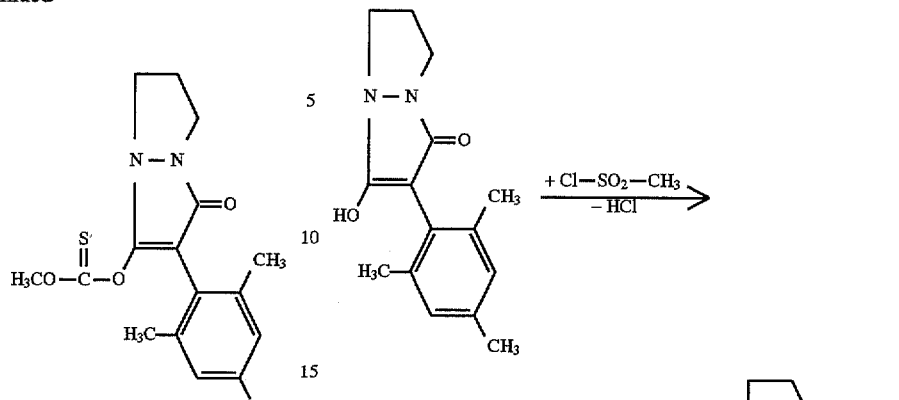

If 3-(2,4,6-trimethylphenyl)-1,5-diaza-bicyclo-(3,3,0$^{1,-5}$) octane-2,4-dione, carbon disulphide and methyl iodide are used as starting components according to process (D-β), the course of the reaction can be represented as follows:

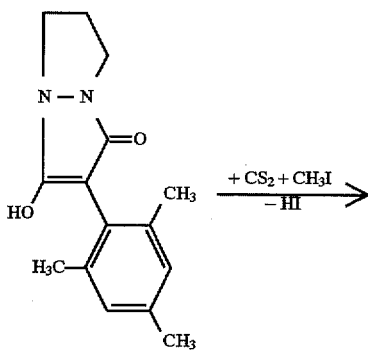

If 3-(2,4,6-trimethylphenyl)-1,5-diaza-bicyclo-(3,3,0$^{1.5}$) nonane-2,4-dione and methanesulphonyl chloride are used as starting materials according to process (E), the course of the reaction can be represented by the following equation:

If 3-(2,4,6-trimethylphenyl)-1,5-diaza-bicyclo-(3,3,0$^{1.5}$) octane-2,4-dione and 2,2,2-trifluoroethyl chloromethanethio-phosphonate are used as starting materials according to process (F), the course of the reaction can be represented by the following equation:

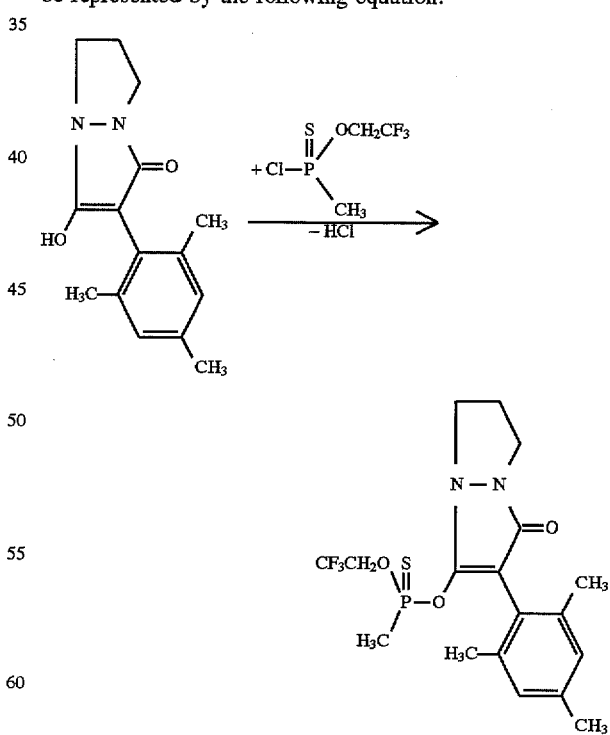

If 3-(2,4,6-trimethylphenyl)-1,5-diaza-bicyclo-(3,3,0$^{1.5}$) octane-2,4-dione and ethyl isocyanate are used as starting substances according to process (G-α), the course of the reaction can be represented by the following equation:

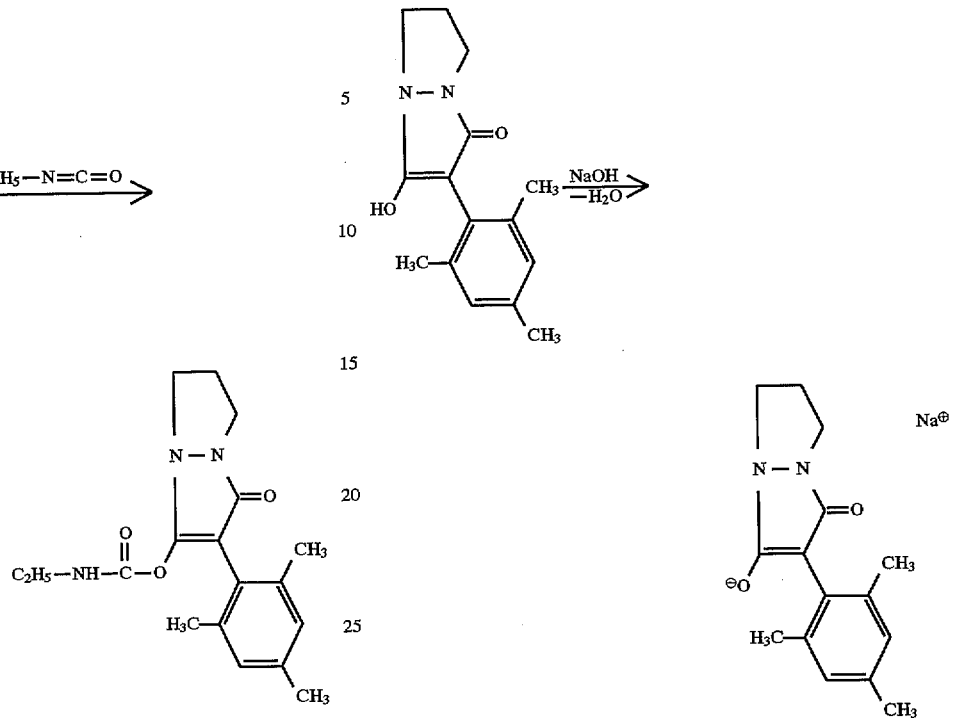

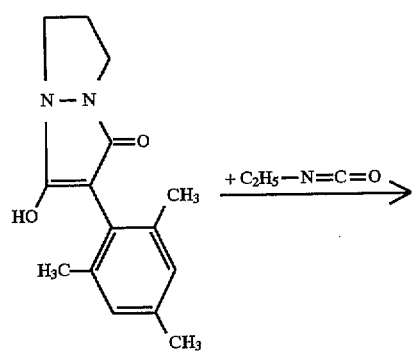

If 3-(2,4,6-trimethylphenyl)-1,5-diaza-bicyclo-(3,3,0$^{1.5}$) octane-2,4-dione and dimethylcarbamoyl chloride are used as starting materials according to process (G-β), the course of the reaction can be represented by the following equation:

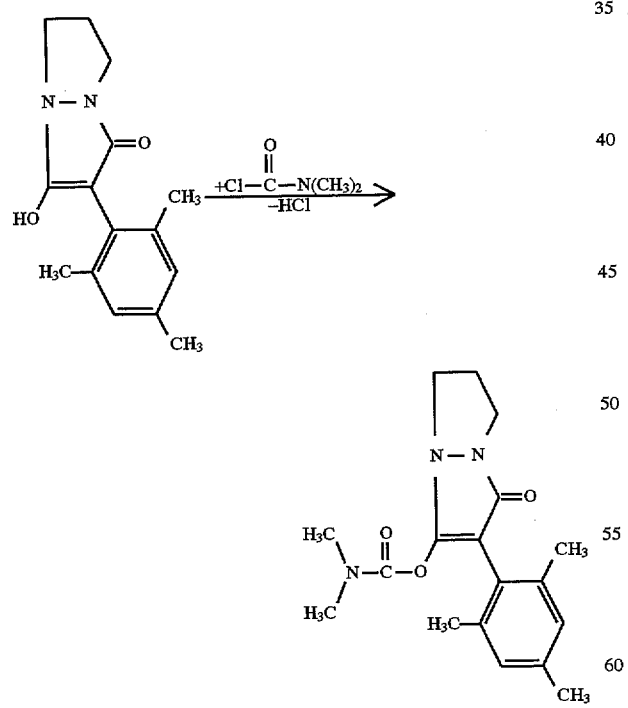

If 3-(2,4,6-trimethylphenyl)-1,5-diaza-bicyclo-(3,3,0$^{1.5}$) octane-2,4-dione and NaOH are used as components according to process (H), the course of the process according to the invention can be represented by the following equation:

Formula (II) provides a general definition of the halogenocarbonyl ketenes required as starting substances for carrying out process (A-α) according to the invention. In this formula (II), X, Y, Z, n and Hal preferably represent those radicals which have already been mentioned in connection with the description of the substances of the formula (I) according to the invention as being preferred for these substituents.

Some of the compounds of the formula (II) are known (cf., for example, Org. Prep. Proced. Int., 7 (4), 155–8, 1975 and DE 1,945,703). However, the compounds which were hitherto unknown can be prepared analogously in a simple manner by methods known in principle. For example, halogenocarbonyl ketones of the formula (II) are obtained when arylmalonic acids of the formula (XVI)

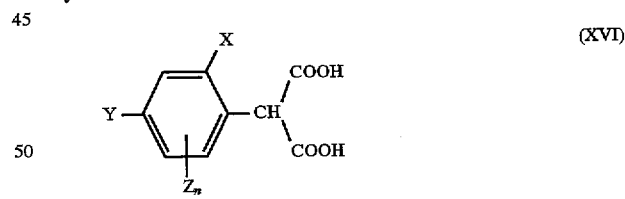

in which

X, Y, Z and n have the abovementioned meaning, are reacted with acid halides such as, for example, thionyl chloride, phosphorus(V) chloride, phosphorus(III) chloride, oxalyl chloride, phosgene or thionyl bromide, if appropriate in the presence of catalysts such as, for example, diethylformamide, methyl-sterylformamide or triphenylphosphine.

The arylmalonic acids of the formula (XVI) are generally known compounds of organic chemistry (cf., for example, Organikum, [Laboratory Practical in Organic Chemistry], VEB Deutscher Verlag der Wissenschaften, Berlin 1977, p. 517 et seq.).

New halogenocarbonyl ketenes can be characterized by formula (IIa)

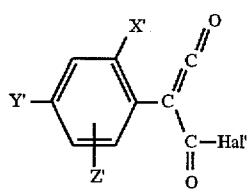

(IIa)

in which

Hal' stands for halogen

X' stands for C$_1$-C$_4$-alkyl, halogen or trifluoromethyl

Y' stands for hydrogen, C$_1$-C$_4$-alkyl, halogen or trifluoromethyl and

Z' stands for hydrogen, C$_1$-C$_4$-alkyl, halogen or trifluoromethyl with the proviso that Z' must not stand for hydrogen, if Y' stands for hydrogen.

Preferred new halogenocarbonyl ketenes are such according to formula (IIa) in which Hal' stands for bromine or chlorine, X' stands for methyl, fluorine, chlorine, bromine or trifluoromethyl, Y' stands for hydrogen, methyl, ethyl, n-propyl, i-propyl, n-butyl, i-butyl, tert-butyl, fluorine, chlorine, bromine or trifluoromethyl and Z' stands for hydrogen, methyl, fluorine, chlorine, bromine or trifluoromethyl with the proviso that Z' must not stand for hydrogen, if Y' stands for hydrogen.

Particularly preferred halogenocarbonyl ketenes are such according to formula (IIa) above, in which X', Y' and Z' either simultaneously stand for methyl or X' and Y' stand for chlorine and Z' simultaneously means hydrogen.

The new halogenocarbonyl ketenes of formula (IIa) in which X', Y', Z' and Hal' have the meanings as defined above can be prepared by reacting arylmalonic acids of the formula (XVIa)

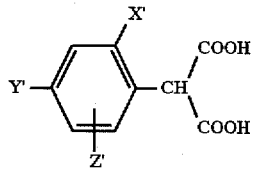

(XVIa)

with acid halides such as, for example, thionyl chloride, phosphorus(V)chloride, phosphorus(III)chloride, oxalyl chloride, phosgene or thionyl bromide, if appropriate in the presence of catalysts such as, for example, diethylformamide, methyl-stearylformamide or triphenylphosphine.

Furthermore the arylmalonic acid starting materials of formula (XIVa) in which X', Y' and Z' have the meaning as defined above are hitherto unknown compounds.

Formula (III) provides a general definition of the malonic ester required as starting substance for carrying out process (A-β) according to the invention. In this formula (III), X, Y, Z and n preferably represent those radicals which have already been mentioned in connection with the description of the substances of the formula (I) according to the invention as being preferred for these substituents.

The arylmalonic esters of the formula (III) are generally known compounds of organic chemistry (cf., for example, Tetrahedron Lett. 27, 2763 (1986) and Organikum, [Laboratory Practical in Organic Chemistry], VEB Deutscher Verlag der Wissenschaften, Berlin 1977, p. 587 et seq.).

Some of the hydrazines of the formula (IV)

A—NH—NH—B           (IV)

in which

A and B have the abovementioned meaning, furthermore required as starting substances for carrying out processes (a-α) and (A-β) according to the invention, are known and/or can be prepared analogously to methods known from the literature (cf., for example, Liebigs Ann. Chem. 585, 6 (1954); Reaktionen der organischen Synthese [Reactions in Organic Synthesis], C. Ferri, page 212, 513; Georg Thieme Verlag Stuttgart, 1978; Liebigs Ann. Chem. 443, 242 (1925); Chem. Ber. 98, 2551 (1965)).

The hydrazines of the formula (IVa)

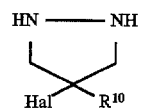

(IVa)

in which

Hal represents fluorine or chlorine and

R$^{10}$ represents optionally halogen-substituted —C$_1$-C$_8$-alkyl, C$_2$-C$_8$-alkenyl or C$_1$-C$_4$-alkoxy-C$_2$-C$_4$-alkyl, which are furthermore required as starting substances for carrying out processes (A-α) and (A-β) according to the invention, are new and the subject of the invention.

The new compounds of the formula (IVa)

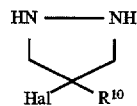

(IVa)

in which

Hal and R$^{10}$ have the abovementioned meaning are obtained when compounds of the formula (XVII)

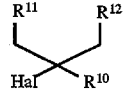

(XVII)

in which

Hal and R$^{10}$ have the abovementioned meaning and

R$^{11}$ and R$^{12}$ represent a suitable leaving group, preferably halogen, in particular chlorine, bromine or iodine, or represent dialkylamino such as, for example, dimethylamino, or in each case optionally substituted alkylsulphonyloxy, alkoxysulphonyloxy or arylsulphonyloxy such as, for example, methanesulphonyloxy, trifluoromethanesulphonyloxy, methoxysulphonyloxy, ethoxysulphonyloxy or p-toluenesulphonyloxy, are reacted with hydrazines at 50° to 150° C (cf. Preparation Example).

The compounds of the formula (XVII) are known (cf., for example, Zh. Org. Khim. 19, 1107 (1983)).

Formula (Ia) provides a general definition of the 4-arylpyrazolidine-3,5-diones or the enols thereof, which are required as starting substances for carrying out processes (B), (C), (D), (E), (F), (G) and (H) according to the invention. In this formula (Ia), A, B, X, Y, Z and n preferably represent those radicals which have already been mentioned in connection with the description of the substances of the formula (I) according to the invention as being preferred for these substituents.

The compounds of the formula (Ia) are new and the subject of the present invention. They can be obtained by process (A).

The acid halides of the formula (V), carboxylic anhydrides of the formula (VI), chloroformic esters or chloroformic thioesters of the formula (VII), chloromonothioformic esters or chlorodithioformic esters of the formula (VIII), alkyl halides of the formula (IX), sulphonyl chlorides of the formula (X), phosphorus compounds of the formula (XI), isocyanates of the formula (XII), carbamoyl chlorides of the formula (XIII) and metal hydroxides or amines of the formula (XIV) and (XV), all of which are furthermore required as starting substances for carrying out processes (B), (C), (D), (E), (F), (G) and (H) according to the invention, are generally known compounds of organic or inorganic chemistry.

Processes (A-α) and (A-β) are characterised in that compounds of the formulae (II) or (III) in which X, Y, Z, n and Hal have the abovementioned meaning and compounds of the formula (IV) in which A and B have the abovementioned meaning, are subjected to a condensation reaction in the presence of bases.

Diluents which can be employed in processes (A-α) and (A-β) according to the invention are all inert organic solvents. The following can preferably be used: hydrocarbons such as toluene and xylene, furthermore ethers such as dibutyl ether, tetrahydrofuran, dioxane, glycol dimethyl ether and diglycol dimethyl ether, moreover polar solvents, such as dimethyl sulphoxide, sulpholane, dimethylformamide and N-methyl-pyrrolidone, and also alcohols such as methanol, ethanol, propanol, isopropanol, butanol, isobutanol and tert-butanol.

Bases (deprotonating agents) which can be employed for carrying out processes (A-α) and (A-β) according to the invention are all customary proton acceptors. The following can preferably be used: the oxides, hydroxides and carbonates of alkali metals and alkaline earth metals such as sodium hydroxide, potassium hydroxide, magnesium oxide, calcium oxide, sodium carbonate, potassium carbonate and calcium carbonate, sodium carbonate, potassium carbonate and calcium carbonate, which can also be employed in the presence of phase transfer catalysts such as, for example, triethylbenzylammonium chloride, tetrabutylammonium bromide, Adogen 464 or TDA 1. Alkali metals such as sodium or potassium can furthermore be used. Moreover, amides and hydrides of alkali metals and Adogen 464= methyltrialkyl($C_8$–$C_{10}$)ammonium chloride TDA 1=tris-(methoxyethoxyethyl)-amine alkaline earth metals such as sodium aide, sodium hydride and calcium hydride, and in addition also alkali metal alcoholates such as sodium methylate, sodium ethylate and potassium tert-butylate, can be employed. When carrying out processes (A-α) and (A-β) according to the invention, the reaction temperatures can be varied within a substantial range. In general, the processes are carried out at temperatures between −20° C. and 250° C., preferably between 0° C. and 150° C.

Processes (A-α) and (A-β) according to the invention are generally carried-out under atmospheric pressure.

When carrying out processes (A-α) and (A-β) according to the invention, the reactants of the formulae (II) and (IV) or (III) and (IV) and the deprotonating bases are generally employed in approximately equimolar amounts. However, it is also possible to use one or the other component in larger excess (up to 3 moles).

Process (B-α) is characterised in that compounds of the formula (Ia) are reacted with carboxylic acid halides of the formula (V).

Diluents which can be employed in process (Bα) according to the invention when acid halides are used are all solvents which are inert to these compounds. The following can preferably be used: hydrocarbons such as benzine, benzene, toluene, xylene and tetralin, furthermore halogenohydrocarbons such as methylene chloride, chloroform, carbon tetrachloride, chlorobenzene and o-dichlorobenzene, furthermore ketones such as acetone and methyl isopropyl ketone, moreover ethers such as diethyl ether, tetrahydrofuran and dioxane, and in addition carboxylic acid esters such as ethyl acetate, and also strongly polar solvents such as dimethyl sulphoxide and sulpholane. If the acid halide is sufficiently stable to hydrolysis, the reaction can also be carried out in the presence of water.

If the corresponding carboxylic acid halides are used, then acid-binding agents which are suitable in the reaction according to process (Bα) according to the invention are all customary acid acceptors. The following can preferably be used: tertiary amines such as triethylamine, pyridine, diazabicyclooctane (DABCO), diazabicycloundecane (DBU), diazabicyclononene (DBN), Hüning base and N,N-dimethyl-aniline, furthermore alkaline earth metal oxides such as magnesium oxide and calcium oxide, furthermore alkali metal carbonates and alkaline earth metal carbonates such as sodium carbonate, potassium carbonate and calcium carbonate.

When carboxylic acid halides are used in process (Bα) according to the invention, the reaction temperatures can also be varied within a substantial range. In general, the process is carried out at temperatures between −20° C. and +150° C., preferably between 0° C. and 100° C.

When carrying out process (B-α) according to the invention, the starting substances of the formula (Ia) and the carboxylic halide of the formula (V) are generally used in approximately equivalent amounts. However, it is also possible to employ the carboxylic anhydride in a larger excess (up to 5 moles). Working-up is carried out by customary methods.

Process (B-β) is characterised in that compounds of the formula (Ia) are reacted with carboxylic anhydrides of the formula (VI).

If carboxylic anhydrides are used as reactants of the formula (VI) in process (B-β) according to the invention, then diluents which can be used are preferably those diluents which are also preferably suitable when acid halides are used. Moreover, a carboxylic hydride employed in excess can also simultaneously act as the diluent.

When carboxylic anhydrides are used in process (B-β) according to the invention, the reaction temperatures can also be varied within a substantial range. In general, the process is carried out at temperatures between −20° C. and +150° C., preferably between 0° C. and 100° C.

When carrying out the process according to the invention, the starting substances of the formula (Ia) and the carboxylic anhydride of the formula (VI) are generally used in approximately equivalent amounts. However, it is also possible to employ the carboxylic anhydride in a larger excess (up to 5 moles). Working-up is carried out by customary methods.

In general, a procedure is followed in which diluent and excess carboxylic anhydride as well as the carboxylic acid which is formed are removed by distillation or by washing with an organic solvent or with water.

Process (C) is characterised in that compounds of the formula (Ia) are reacted with chloroformic esters or chloroformic thioesters of the formula (VII).

If the corresponding chloroformic esters or chloroformic thioesters are used, then acid-binding agents which are suitable in the reaction according to process (C) according to the invention are all customary acid acceptors. The following can preferably be used: tertiary amines such as triethylamine, pyridine, DABCO, DBU, DBA, Hüning base and N,N-dimethyl-aniline, furthermore alkaline earth metal oxides such as magnesium oxide and calcium oxide, moreover alkali metal carbonates and alkaline earth metal carbonates such as sodium carbonate, potassium carbonate and calcium carbonate.

When the chloroformic esters or chloroformic thioesters are used in process (C) according to the invention, then diluents which can be employed are all solvents which are inert to these compounds. The following can preferably be used: hydrocarbons such as benzine, benzene, toluene, xylene and tetralin, furthermore halogenohydrocarbons such as methylene chloride, chloroform, carbon tetrachloride, chlorobenzene and o-dichlorobenzene, furthermore ketones such as acetone and methyl isopropyl ketone, moreover ethers such as diethyl ether, tetrahydrofuran and dioxane, in addition carboxylic acid esters such as ethyl acetate, and also strongly polar solvents such as dimethyl sulphoxide and sulpholane.

When the chloroformic esters or chloroformic thioesters are used as carboxylic acid derivatives of the formula (VII), the reaction temperatures at which process (C) according to the invention is carried out can be varied within a substantial range. If the process is carried out in the presence of a diluent and of an acid-binding agent, then the reaction temperatures are generally between −20° C. and +100° C., preferably between 0° C. and 50° C.

Process (C) according to the invention is generally carried out under atmospheric pressure.

When carrying out process (C) according to the invention, the starting substances of the formula (Ia) and the corresponding chloroformic ester or chloroformic thioester of the formula (VII) are generally used in approximately equivalent amounts. However, it is also possible to employ one or the other component in a larger excess (up to 2 moles). Working-up is then carried out by customary methods. In general, a procedure is followed in which precipitated salts are removed and the reaction mixture which remains is concentrated by stripping off the diluent.

In preparation process (D-α), approx. 1 mole of chloromonothioformic ester or chlorodithioformic ester of the formula (VII) is reacted per mole of starting compound of the formula (Ia) at 0° to 120° C., preferably at 20° to 60° C.

Suitable diluents which may be added are all inert polar organic solvents such as ethers, aides, alcohols, sulphones or sulphoxides.

Dimethyl sulphoxide, tetrahydrofuran, dimethylformamide and dimethyl sulphide are preferably employed.

If, in a preferred embodiment, the enolate salt of the compound Ia is synthesised by adding strong deprotonating agents such as, for example, sodium hydride or potassium tertiary butylate, a further addition of acid-binding agents can be dispensed with.

If acid-binding agents are employed, then customary inorganic or organic bases are suitable, sodium hydroxide, sodium carbonate, potassium carbonate, pyridine or triethylamine being mentioned by way of example.

The reaction can be carried out under atmospheric pressure or under increased pressure; it is preferably carried out under atmospheric pressure. Working-up is carried out by customary methods.

In preparation process (D-β), an equimolar amount or an excess of carbon disulphide is added per mole of starting compound of the formula (Ia). This is preferably carried out at temperatures of 0° to 50° C. and, in particular at 20° to 30° C.

It is often expedient first to prepare the corresponding salt from the compound of the formula (Ia) by adding a deprotonating agent (such as, for example, potassium tertiary butylate or sodium hydride). Compound (Ia) is reacted with carbon disulphide until the formation of the intermediate is complete, for example after stirring at room temperature for several hours.

The further reaction with the alkyl halide of the formula (IX) is preferably carried out at 0° to 70° C. and, in particular at 20° to 50° C. In this process, at least the equimolar amount of alkyl halide is employed.

The process is carried out under atmospheric pressure or under increased pressure, preferably under atmospheric pressure.

Again, working-up is carried out by customary methods.

In preparation process (E), approx. 1 mole of sulphonyl chloride (X) is reacted per mole of starting compound the formula (Ia) at 0° to 150° C., preferably at 20° to 70° C.

Suitable diluents which may be added are all inert polar organic solvents such as ethers, amides, nitriles, alcohols, sulphones or sulphoxides.

Dimethyl sulphoxide, tetrahydrofuran, dimethylformamide or dimethyl sulphide are preferably employed.

If, in a preferred embodiment, the enolate salt of the compound Ia is synthesised by adding strong deprotonating agents (such as, for example, sodium hydride or potassium tertiary butylate), a further addition of acid-binding agents can be dispensed with.

If acid-binding agents are employed, then customary inorganic or organic bases are suitable, sodium hydroxide, sodium carbonate, potassium carbonate and pyridine being mentioned by way of example.

The reaction can be carried out under atmospheric pressure or under increased pressure; it is preferably carried out under atmospheric pressure. Working-up is carried out by customary methods.

If appropriate, preparation process (E) can be carried out under phase-transfer conditions (W. J. Spillane et al.; J. Chem. Soc., Perkin Trans I, (3) 677–9 (1982)). In this case, 0.3 to 1.5 moles of sulphonyl chloride (X), preferably 0.5 mole, are reacted at 0° to 150° C., preferably at 20° to 70° C., per mole of starting compound of the formula Ia).

Phase-transfer catalysts which can be used are all quaternary ammonium salts, preferably tetraoctylammonium bromide and benzyltriethylammonium chloride. Organic solvents which can be used in this case are all nonpolar inert solvents, the use of benzene and toluene being preferred.

To obtain compounds of the structure (Ie), 1 to 2, preferably 1 to 1.3, moles of the phosphorus compound of the formula (XI) are reacted in preparation process (F) at temperatures between −40° C. and 150° C., preferably between −10° and 110° C.

Suitable diluents which may be added are all inert, polar organic solvents such as ethers, amides, nitriles, alcohols, sulphides, sulphones or sulphoxides, inter alia.

Acetonitrile, dimethyl sulphoxide, tetrahydrofuran, dimethylformamide and dimethyl sulphide are preferably employed.

Suitable acid-binding agents which may be added are customary organic or inorganic bases such as hydroxides or carbonates. The following may be mentioned by way of example: sodium hydroxide, sodium carbonate, potassium carbonate and pyridine.

The reaction can be carried out tinder atmospheric pressure or under increased pressure; it is preferably carried out under atmospheric pressure. Working-up is carried out by customary methods of organic chemistry. The end products obtained are preferably purified by crystallisation, chromatographic purification or by so-called "incipient distillation", that is to say, removal of the volatile components in vacuo.

In preparation process (G-α), approx. 1 mole of isocyanate of the formula (XII) is reacted per mole of starting compound of the formula (Ia) at 0° to 100° C., preferably at 20° to 50° C.

Suitable diluents which may be added are all inert organic solvents such as ethers, amides, nitriles, sulphones and sulphoxides.

If appropriate, catalysts can be added to accelerate the reaction. Catalysts which can be employed very advantageously are organotin compounds such as, for example, dibutyltin dilaurate. The reaction is preferably carried out under atmospheric pressure.

In preparation process (G-β), approx. 1 mole of carbamoyl chloride or thiocarbamoyl chloride of the formula (XIII) is reacted per mole of starting compound of the formula (Ia) at 0° to 150° C., preferably at 20° to 70° C.

Suitable diluents which may be added are all inert polar organic solvents such as ethers, amides, alcohols, sulphones and sulphoxides.

Dimethyl sulphoxide, tetrahydrofuran, dimethylformamide and dimethyl sulphoxide are preferably employed.

If, in a preferred embodiment, the enolate salt of the compound of the formula (Ia) is synthesised by adding strong deprotonating agents (such as, for example, sodium hydride or potassium tertiary butylate), a further addition of acid-binding agents can be dispensed with.

If acid-binding agents are employed, then customary inorganic or organic bases are suitable, sodium hydroxide, sodium carbonate, potassium carbonate and pyridine being mentioned by way of example.

The reaction can be carried out under atmospheric pressure or under increased pressure; it is preferably carried out under atmospheric pressure. Working-up is carried out by customary methods.

Process (H) is characterised in that compounds of the formula (Ia) are reacted with metal hydroxides (XIV) or amines (XV).

Diluents which can be employed in the process according to the invention are preferably ethers such as tetrahydrofuran, dioxane, diethyl ether, or else alcohols such as methanol, ethanol or isopropanol, but also water. Process (H) according to the invention is generally carried out under atmospheric pressure. The reaction temperatures are generally between −20° C. and 100° C., preferably between 0° C. and 50° C.

When carrying out the process (H) according to the invention, the starting substances of the formula (Ia) or (XIV) or (XV) are generally used in approximately equimolar amounts. However, it is also possible to employ one or the other component in a larger excess (up to 2 moles). In general, a procedure is followed in which the reaction mixture is concentrated by stripping off the diluent.

The active compounds are suitable for combating animal pests preferably arthropods and nematodes, in particular insects and arachnids, encountered in agriculture, in forestry, in the protection of stored products and materials, and in the hygiene sector. They are active against normally sensitive and resistant species and against all or some stages of development. The abovementioned pests include:

From the order of the isopoda, for example, *Oniscus asellus, Armadillidium vulgare* and *Porcellio scaber*.

From the order of the Diplopoda, for example, *Blaniulus guttulatus*.

From the order of the Chilopoda, for example, *Geophilus carpophagus* and *Scutigera* spec.

From the order of the Symphyla, for example, *Scutigerella immaculata*.

From the order of the Thysanura, for example, *Lepisma saccharina*.

From the order of the Collembola, for example, *Onychiurus armatus*.

From the order of the Orthoptera, for example, *Blatta orientalis, Periplaneta americana, Leucophaea maderae, Blattella germanica, Acheta domesticus*, Gryllotalpa spp., *Locusta migratoria migratorioides*, Melanoplus differentialis and *Schistocerca gregaria*.

From the order of the Dermaptera, for example, *Forficula auricularia*.

From the order of the Isoptera, for example, Reticulitermes spp.

From the order of the Anoplura, for example, *Phylloxera vastatrix*, Pemphigus spp., *Pediculus humanus corporis*, Haematopinus spp. and Linognathus spp.

From the order of the Mallophaga, for example, Trichodectes spp. and Damalinea spp.

From the order of the Thysanoptera, for example, *Hercinothrips femoralis* and *Thrips tabaci*.

From the order of the Heteroptera, for example, Eurygaster spp., *Dysdercus intermedius, Piesma quadrata, Cimex lectularius, Rhodnius prolixus* and Triatoma spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Doralis pomi, Eriosoma lanigerum, Hyalopterus arundinis, Macrosiphum avenae*, Myzus spp., *Phorodon humuli, Rhopalosiphum padi*, Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae*, Pseudococcus spp. Psylla spp.

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea, Lymantria* spp. *Bucculatrix thurberiella, Phyllocnistis citrella*, Agrotis spp., Euxoa spp., Feltia spp., *Earias insulana*, Heliothis spp., *Spodoptera exigua, Mamestra brassicae, Panolis flammea, Prodenia litura*, Spodoptera spp., Trichoplusia ni, *Carpocapsa pomonella*, Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana*.

From the order of the Coleoptera, for example, *Anobium punctatum, Rhizopertha dominica, Acanthoscelides obtectus, Acanthoscelides obtectus, Hylotrupes bajulus, Agelastica alni, Leptinotarsa decemlineata, Phaedon cochleariae*, Diabrotica spp., *Psylliodes chrysocephala, Epilachna varive stis*, Atomaria spp., *Oryzaephilus surinamensis, Antho nomus* spp., Sitophilus spp., *Otiorrhynchus sulcatus, Cosmopolites sordidus, Ceuthorrhynchus assimilis, Hypera postica*, Dermestes spp., Trogoderma spp., Anthrenus spp., Attagenus spp., Lyctus spp., *Meligethes aeneus*, Ptinus spp., *Niptus hololeucus, Gibbium psylloides*, Tribolium spp., *Tenebrio molitor*, Agriotes spp., *Cono derus* spp., *Melolontha melolontha, Amphimallon solsti tialis* and *Costelytra zealandica*.

From the order of the Hymenoptera, for example, Diprion spp., Hoplocampa spp., Lasius spp., *Monomorium pharaonis* and Vespa spp.

From the order of the Diptera, for example, Aedes spp., Anopheles spp., Culex spp., *Drosophila melanogaster*, Musca spp., Fannia spp., *Calliphora erythrocephala*, Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit*, Phorbia spp., *Pegomyia hyoscyami, Ceratitis capitata, Dacus oleae* and *Tipula paludosa*.

From the order of the Siphonaptera, for example, *Xenopsylla cheopis* and Ceratophyllus spp.

From the order of the Arachnida, for example, *Scorpio maurus* and *Latrodectus mactans*.

From the order of the Acarina, for example, *Acarus siro*, Argas spp., Ornithodoros spp., *Dermanyssus gallinae, Eriophyes ribis, Phyllocoptruta oleivora*, Boophilus spp., Rhipicephalus spp., Amblyomma spp., Hyalomma spp., Ixodes spp., Psoroptes spp., Chorioptes spp., Sarcoptes spp. and Tarsonemus spp., *Bryobia praetiosa*, Panonychus spp. Tetranychus spp.

The active compounds according to the invention are distinguished by a high insecticidal and acaricidal activity.

They can be employed with particularly good success for combating insects which damage plants, such as, for example, against the caterpillars of the cabbage moth (*Plutella maculipennis*) or against mites which damage plants such as, for example, against the greenhouse red spider mite or the two-spotted spider mite (*Tetranychus urticae*).

In addition, the active compounds according to the invention also show a nematicidal action.

The active compounds according to the invention are not only active against plant, hygiene and stored product pests, but also, in the veterinary medicine sector, against animal parasites (ectoparasites and endoparasites), such as scaly ticks, argasidae, scab mites, trombidae, flies (stinging and sucking), parasitic fly larvae, lice, hair lice, bird lice, fleas and worms which live as endoparasites.

They are active against normally sensitive and resistant species and strains, as well as against all parasitic and non-parasitic stages of development of the ecto- and endoparasites.

The compound according to the invention also exhibit an effectiveness against protozoen and especially a coccidiostatic effectiveness.

The active compounds according to the invention can furthermore be used as defoliants, desiccants, agents for destroying broad-leaved plants and, especially, as weedkillers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus and Taraxacum.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticuun, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, on lawns, turf and pasture-land, and for the selective combating of weeds in annual cultures.

The active compounds according to the invention are highly suitable for selectively combating monocotyledon weeds in dicotyledon cultures by the pre- and post-emergence method. For example, they can be employed highly successfully in soybeans or sugar beet for combating grass weeds.

The active compounds can be converted into the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in a known manner; for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene, or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silica, alumina and silicates, as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example lignin-sulphite waste liquors and methylcellulose.

Adhesives such as carboxymethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95% by weight of active compound, preferably between 0.5 and 90%.

For combating weeds, the active compounds according to the invention, as such or in the form of their formulations, can also be used as mixtures with known herbicides, finished formulations or tank mixes being possible.

Suitable herbicides for the mixtures are known herbicides, such as, for example, 1-amino-6-ethylthio-3-(2,2-dimethylpropyl)-1,3,5-triazine-2,4(1H,3H)-dione (AMETHYDIONE) or N-(2-benzothiazolyl)-N,N'-dimethyl-urea (METABENZTHIAZURON) for combating weeds in cereals; 4-amino-3-methyl-6-phenyl-1,2,4-triazin-5(4H)-one (METAMITRON) for combating weeds in sugar beet and 4-amino-6-(1,1-dimethylethyl)-3-methylthio-1,2,4-triazin-5(4H)-one (METRIBUZIN) for combating weeds in soya beans. Other suitable compounds are 5-(2-chloro-4-trifluoromethyl-phenoxy)-2-nitro-benzoic acid (ACIFLUORFEN); 3-isopropyl-2,1,3-benzothiadiazin-4-one 2,2-dioxide (BENTAZONE); methyl 5-(2,4-dichlorophenoxy)-2-nitro-benzoate (BIFENOX); 5-amino-4-chloro-2-phenyl-2,3-dihydro-3-oxy-pyridazine (CHLORIDAZON); ethyl 2-{[(4-chloro-6-methoxy-2-pyrimidinyl)-aminocarbonyl]aminosulphonyl}-benzoate (CHLORIMURON); 4-amino-6-t-butyl-3-ethylthio-1,2,4-triazin-5(4H)-one (ETHIOZIN); 5-(2-chloro-4-trifluoromethyl-phenoxy)-N-methylsulphonyl-2-nitrobenzamide (FOMESAFEN); 2-[5-methyl-5-(1-methylethyl)-4-oxo-2-imidazolin-2-yl]-3-quinolinecarboxylic acid (IMAZAQUIN); N-methyl-2-(1,3-benzothiazol-2-yloxy)acetanilide (MEFENACET); 1-(3-trifluoromethyl-phenyl)-4-methylamino-5-chloro-6-pyridazone (NORFLURAZON); N-(1-ethylpropyl)-3,4-dimethyl-2,6-dinitroaniline (PENDIMETHALIN); 3-(ethoxycarbonylaminophenyl) N-(3'-methylphenyl) carbamate (PHENMEDIPHAM); methyl 3-[[[[(4-methoxy-6-methyl-1,3,5-triazin-2-yl)-amino]-carbonyl]-amino]-sulphonyl]-thiophene-2-carboxylate (THIAMETURON); 2,6-dinitro-4-trifluoromethyl-N,N-dipropylaniline (TRIFLURALIN). Surprisingly, some mixtures also show a synergistic action.

Mixtures with other known active compounds, such as fungicides, insecticides, acaricides, nematicides, bird repellants, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomising or scattering.

The active compounds according to the invention can be applied either before or after emergence of the plants.

They can also be incorporated into the soil before sowing.

The amount of active compound used can vary within a substantial range. It depends essentially on the nature of the desired effect. In general, the amounts used are between 0.01 and 10 kg of active compound per hectare of soil surface, preferably between 0.05 and 5 kg per ha.

The preparation and use of the active compounds according to the invention can be seen from the following examples.

PREPARATION EXAMPLES

Example 1

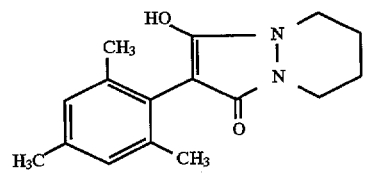

22.5 g (0.1 mol) of mesityl chlorocarbonyl ketene are initially introduced into 200 ml of ether, and, at 20° C., the mixture is treated with 8.7 g (0.1 mol of piperidazine, 16.5 ml (0.11 mol) of triethylamine and 10 ml of ether. The mixture is stirred for one day at 50° C., the hydrochloride which has formed is filtered off, and the solvent is distilled off under a water pump vacuum. The residue is subsequently taken up in 50 ml of tetrahydrofuran, and this solution is stirred into 1,000 ml of an HCl/ice-mixture. After the solid has been filtered off with suction and then dried, 18.4 g (66% of theory) of 3-hydroxy-4-mesityl-5-oxo-1,2-tetramethylenepyrazoline of melting point 190° C. are obtained.

Example 2

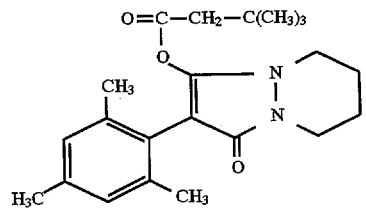

27.3 g (0.1 mol) of 3-hydroxy-4-mesityl-5-oxo-1,2-tetramethylenelpyrazoline and 30 ml of triethylamine (0.2 mol) are dissolved in 500 ml of tetrahydrofuran, and the solution is treated, at a temperature of 20° C., with 13 g (0.12 mol) of 3,3-dimethylbutyryl chloride. The reaction mixture is stirred for 4 hours at 40° C. and then poured into 1,000 ml of water. The solid which has formed is filtered off with suction and dried.

34 g (92% of theory) of 5-oxo-3-neopentyl-carbonyloxy-4-mesityl-1,2-tetramethylene-pyrazoline of melting point 76° C. are obtained.

The end products of the formula (I)

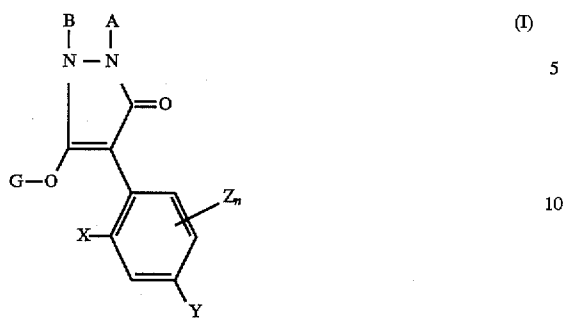

(I)

which are listed below in Table 1 are obtained analogously to Example 1 and 2 taking into account the information in the description of the processes according to the invention.

TABLE 1

| Example No. | X | Y | $Z_n$ | G | A | B | physical data (m.p.) |
|---|---|---|---|---|---|---|---|
| 3 | $CH_3$ | $CH_3$ | 2-$CH_3$ | $-CO-C(CH_3)_3$ | | $-(CH_2)_4-$ | wax |
| 4 | $CH_3$ | $CH_3$ | 2-$CH_3$ | $-COOCH(CH_3)_2$ | | $-(CH_2)_4-$ | wax |
| 5 | $CH_3$ | $CH_3$ | 2-$CH_3$ | $-COOC_2H_5$ | | $-(CH_2)_4-$ | wax |
| 6 | $CH_3$ | $CH_3$ | 2-$CH_3$ | H | H | $C_6H_5$ | >230° C. |
| 7 | $CH_3$ | $CH_3$ | 2-$CH_3$ | $-\underset{\underset{S}{\|}}{C}-N(CH_3)_2$ | | $-(CH_2)_4$ | 124° C. |
| 8 | $CH_3$ | $CH_3$ | 2-$CH_3$ | $-\underset{\underset{S}{\|}}{P}\underset{CH_3}{\overset{OCH_3}{<}}$ | | $-(CH_2)_4-$ | 137° C. |
| 9 | $CH_3$ | $CH_3$ | 2-$CH_3$ | $-\underset{\underset{S}{\|}}{P}\underset{C_2H_5}{\overset{OCH_3}{<}}$ | | $-(CH_2)_4-$ | wax |
| 10 | $CH_3$ | $CH_3$ | 2-$CH_3$ | $-CO-\underset{\underset{CH_2}{\|}}{\overset{CH_3}{\overset{\|}{C}}}-C_2H_5$ | | $-(CH_2)_4-$ | 120° C. |
| 11 | $CH_3$ | $CH_3$ | 2-$CH_3$ | $-CO-CH(CH_3)_2$ | | $-(CH_2)_4-$ | wax |
| 12 | $CH_3$ | $CH_3$ | 2-$CH_3$ | $-\underset{\underset{O}{\|}}{P}\underset{SCH-C_2H_5}{\overset{OC_2H_5}{<}}\underset{CH_3}{\|}$ | | $-(CH_2)_4-$ | oil |
| 13 | $CH_3$ | $CH_3$ | 2-$CH_3$ | $-CO\underset{\underset{CH_3}{\|}}{\overset{CH_3}{\overset{\|}{C}}}CH_2CH_2Cl$ | | $-(CH_2)_4-$ | m.p.: 136° C. |
| 14 | $CH_3$ | $CH_3$ | 2-$CH_3$ | H | | $-CH_2CF-CH_2-$<br>$\quad\quad\quad\|$<br>$\quad\quad\,CH_3$ | m.p.: 220° C. |
| 15 | $CH_3$ | $CH_3$ | 2-$CH_3$ | $-COSC_2H_5$ | | $-(CH_2)_4-$ | $n_D^{20}$: 1.3330 |
| 16 | $CH_3$ | $CH_3$ | 2-$CH_3$ | $-CON(CH_3)_2$ | | $-(CH_2)_4-$ | m.p.: 150° C. |
| 17 | $CH_3$ | $CH_3$ | 2-$CH_3$ | $-CO\underset{\underset{CH_3}{\|}}{\overset{CH_3}{\overset{\|}{C}}}-C_2H_5$ | | $-CH_2CF_2CH_2-$ | $n_D^{20}$: 1.5190 |
| 18 | $CH_3$ | $CH_3$ | 2-$CH_3$ | $-COCH_3$ | | $-CH_2CF-CH_2-$<br>$\quad\quad\quad\|$<br>$\quad\quad\,CH_3$ | m.p.: 107° C. |
| 19 | $CH_3$ | $CH_3$ | 2-$CH_3$ | $-COC(CH_3)_3$ | | $-CH_2CF-CH_2-$<br>$\quad\quad\quad\|$<br>$\quad\quad\,CH_3$ | m.p.: 128° C. |

TABLE 1-continued

| Example No. | X | Y | $Z_n$ | G | A | B | physical data (m.p.) |
|---|---|---|---|---|---|---|---|
| 20 | $CH_3$ | $CH_3$ | 2-$CH_3$ | H | \multicolumn{2}{c|}{—$(CH_2)_3$—} | m.p.: 98° C. |
| 21 | $CH_3$ | $CH_3$ | 2-$CH_3$ | —COOCH(CH$_2$OC$_2$H$_5$)—CH$_3$ | \multicolumn{2}{c|}{—CH$_2$CF(CH$_3$)—CH$_2$—} | m.p.: 73° C. |
| 22 | $CH_3$ | $CH_3$ | 2-$CH_3$ | —COCH$_2$C(CH$_3$)$_2$—CH$_3$ | \multicolumn{2}{c|}{—CH$_2$CF(CH$_3$)—CH$_2$—} | m.p.: 105° C. |
| 23 | $CH_3$ | $CH_3$ | 2-$CH_3$ | —COCH$_2$C(CH$_3$)$_2$—CH$_3$ | \multicolumn{2}{c|}{—$(CH_2)_3$—} | m.p.: 89° C. |
| 24 | $CH_3$ | $CH_3$ | 2-$CH_3$ | —COC(CH$_3$)$_2$—CH(CH$_3$)$_2$ | \multicolumn{2}{c|}{—$(CH_2)_4$—} | m.p.: 95° C. |
| 25 | $CH_3$ | $CH_3$ | 2-$CH_3$ | —CO—C(CH$_3$)$_3$ | \multicolumn{2}{c|}{—$(CH_2)_3$—} | m.p.: 108° C. |
| 26 | $CH_3$ | $CH_3$ | 2-$CH_3$ | —CO—C(CH$_3$)$_3$ | \multicolumn{2}{c|}{—CH$_2$CF$_2$CH$_2$—} | $n_D^{20}$: 1,5077 |
| 27 | $CH_3$ | $CH_3$ | 2-$CH_3$ | —COCH$_3$ | H | $C_6H_5$ | m.p.: 158° C. |
| 28 | $CH_3$ | $CH_3$ | 2-$CH_3$ | —COCH$_2$C(CH$_3$)$_3$ | H | $C_6H_5$ | m.p.: 176° C. |
| 29 | $CH_3$ | $CH_3$ | 2-$CH_3$ | —COC(CH$_3$)$_3$ | H | $C_6H_5$ | m.p.: 179° C. |
| 30 | $CH_3$ | $CH_3$ | 2-$CH_3$ | H | \multicolumn{2}{c|}{—CH$_2$—(norbornyl)—CH$_2$—} | m.p.: >200° C. |
| 31 | $CH_3$ | $CH_3$ | 2-$CH_3$ | H | \multicolumn{2}{c|}{—CH$_2$CF$_2$CH$_2$—} | m.p.: 208° C. |
| 32 | $CH_3$ | $CH_3$ | 2-$CH_3$ | —COCH$_2$C(CH$_3$)$_2$—CH$_3$ | \multicolumn{2}{c|}{—CH$_2$CF$_2$CH$_2$—} | m.p.: 32° C. |
| 33 | $CH_3$ | $CH_3$ | 2-$CH_3$ | —COCH$_3$ | \multicolumn{2}{c|}{—CH$_2$CF$_2$CH$_2$—} | $n_D^{20}$: 1,5402 |
| 34 | $CH_3$ | $CH_3$ | 2-$CH_3$ | —COOCH(CH$_3$)—CH$_2$O(CH$_3$) | \multicolumn{2}{c|}{—CH$_2$CF$_2$CH$_2$—} | $n_D^{20}$: 1,4995 |
| 35 | $CH_3$ | $CH_3$ | 2-$CH_3$ | —COC(CH$_3$)$_2$—CH(CH$_3$)$_2$ | \multicolumn{2}{c|}{—CH$_2$CF$_2$CH$_2$—} | $n_D^{20}$: 1,5062 |
| 36 | $CH_3$ | $CH_3$ | 2-$CH_3$ | —SO$_2$CH$_3$ | \multicolumn{2}{c|}{—$(CH_2)_4$—} | m.p.: 120° C. |
| 37 | $CH_3$ | $CH_3$ | 6-$CH_3$ | H | H | cyclohexyl | 138° C. |
| 38 | $CH_3$ | $CH_3$ | 6-$CH_3$ | —C(=O)—O—CH(CH$_3$)—CH$_2$—OC$_2$H$_5$ | \multicolumn{2}{c|}{cyclopentyl} | $n_D^{20}$: 1.5371 |
| 39 | $CH_3$ | $CH_3$ | 6-$CH_3$ | —C(=O)—C(CH$_3$)$_2$—CH(CH$_3$)$_2$ | \multicolumn{2}{c|}{cyclopentyl} | 149° C. |
| 40 | $CH_3$ | $CH_3$ | 6-$CH_3$ | —C(=O)—C(CH$_3$)$_2$—C$_2$H$_5$ | \multicolumn{2}{c|}{cyclopentyl} | 140° C. |

TABLE 1-continued

| Example No. | X | Y | $Z_n$ | G | A | B | physical data (m.p.) |
|---|---|---|---|---|---|---|---|
| 41 | CH₃ | CH₃ | 6-CH₃ | —C(=O)—CH₃ |  | | 156° C. |
| 42 | CH₃ | CH₃ | 6-CH₃ | —C(=O)—C(CH₃)₃ |  | | 86° C. |
| 43 | CH₃ | CH₃ | 6-CH₃ | —C(=O)—C(CH₃)₂—CH(CH₃)₂ | H | 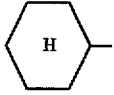 | 181° C. |
| 44 | CH₃ | CH₃ | 6-CH₃ | —C(=O)—O—CH(CH₃)—CH₂—OC₂H₅ | H | 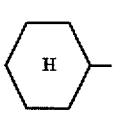 | 80° C. |
| 45 | CH₃ | CH₃ | 6-CH₃ | —C(=O)—C(CH₃)₂—C₂H₅ | H | 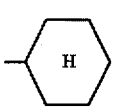 | 192° C. |
| 46 | CH₃ | CH₃ | 6-CH₃ | H | —(CH₂)₅— | | >220° C. |
| 47 | CH₃ | CH₃ | 6-CH₃ | H | —CH₂-C(CH₃)₂-CH₂— | | >200° C. |
| 48 | CH₃ | CH₃ | 6-CH₃ | —C(=O)—CH₂—C(CH₃)₃ | —CH₂-C(CH₃)₂-CH₂— | | 55° C. |
| 49 | CH₃ | CH₃ | 6-CH₃ | —C(=O)—C(CH₃)₂—C₂H₅ | —(CH₂)₅— | | 125° C. |
| 50 | CH₃ | CH₃ | 6-CH₃ | —C(=O)—CH₃ | —(CH₂)₅— | | 130° C. |
| 51 | CH₃ | CH₃ | 6-CH₃ | H | —CH(CH₃)—CH₂-CH(CH₃)— | | 158° C. |
| 52 | CH₃ | CH₃ | 6-CH₃ | H | H | CH₃ | 210° C. |
| 53 | CH₃ | CH₃ | 6-CH₃ | —C(=O)—C(CH₃)₃ | H | CH₃ | 158° C. |
| 54 | CH₃ | CH₃ | 6-CH₃ | —C(=O)—C(CH₃)₂—C₂H₅ | H | CH₃ | 184° C. |
| 55 | CH₃ | CH₃ | 6-CH₃ | —C(=O)—CH₂—C(CH₃)₃ | H | CH₃ | 36° C. |
| 56 | CH₃ | CH₃ | 6-CH₃ | —C(=O)—CH₃ | H | CH₃ | 82° C. |
| 57 | CH₃ | CH₃ | 6-CH₃ | —C(=O)—C(CH₃)₃ | —CH(CH₃)—CH₂-CH(CH₃)— | | 60° C. |
| 58 | CH₃ | CH₃ | 6-CH₃ | —C(=O)—CH₃ | —CH(CH₃)—CH₂-CH(CH₃)— | | 136° C. |
| 59 | CH₃ | CH₃ | 6-CH₃ | —C(=O)—C(CH₃)₂—CH(CH₃)₂ | —CH(CH₃)—CH₂-CH(CH₃)— | | 78° C. |
| 60 | CH₃ | CH₃ | 6-CH₃ | —C(=O)—CH₂—C(CH₃)₃ | —CH(CH₃)—CH₂-CH(CH₃)— | | 76° C. |
| 61 | CH₃ | CH₃ | 6-CH₃ | —C(=O)—C(CH₃)₂—C₂H₅ | —CH(CH₃)—CH₂-CH(CH₃)— | | 120° C. |

TABLE 1-continued

| Example No. | X | Y | $Z_n$ | G | A | B | physical data (m.p.) |
|---|---|---|---|---|---|---|---|
| 62 | $CH_3$ | $CH_3$ | 6-$CH_3$ | $-\underset{\underset{O}{\|}}{C}-C(CH_3)_3$ | $-CH_2-\underset{\underset{CH_3}{\|}}{C(C_3H_7)}-CH_2-$ | | 91° C. |
| 63 | $CH_3$ | $CH_3$ | 6-$CH_3$ | $-\underset{\underset{O}{\|}}{C}-C(CH_3)_2-CH(CH_3)_2$ | $-CH_2-\underset{\underset{CH_3}{\|}}{C(C_3H_7)}-CH_2-$ | | 76° C. |
| 64 | $CH_3$ | $CH_3$ | 6-$CH_3$ | $-\underset{\underset{O}{\|}}{C}-C(CH_3)_3$ | $-CH_2-CH_2-\underset{\underset{CH_3}{\|}}{CH}-$ | | 125° C. |
| 65 | $CH_3$ | $CH_3$ | 6-$CH_3$ | $-\underset{\underset{O}{\|}}{C}-C(CH_3)_2-CH(CH_3)_2$ | $-CH_2-CH_2-\underset{\underset{CH_3}{\|}}{CH}-$ | | 119° C. |
| 66 | $CH_3$ | $CH_3$ | 6-$CH_3$ | $-\underset{\underset{O}{\|}}{C}-CH_3$ | $-CH_2-\underset{\underset{CH_3}{\|}}{C(C_3H_7)}-CH_2-$ | | |

Preparation of the starting compounds

Example (II-1)

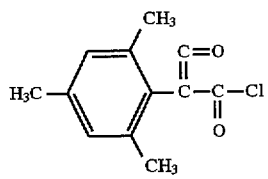

444.5 g (2 mol) of mesitylmalonic acid are suspended in 1,000 ml of methylcyclohexane at 75°–80° C., and 714 g (6 mol) of thionyl chloride are added dropwise in the course of 3 hours. The mixture is then slowly heated further and stirring of the refluxed mixture is continued for 8 hours at a bath temperature of 110°–120° C., Excess thionyl chloride is distilled off together with the solvent at a bath temperature of up to 80° C. at 10 mbar, the cold residue is diluted with the 3-fold amounts of petroleum ether, and the mixture is filtered, concentrated and distilled.

373 g (84% of theory) of mesitylchlorocarbonyl ketene of boiling point 96°/0.45 mbar are obtained.

The starting compounds of the formula (II)

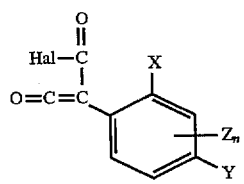

listed below in Table 2 are obtained analogously to Example (II-1) taking into consideration the information in the description of the processes according to the invention:

| Ex. No. | X | Y | $Z_n$ | Physical constant b.p. [°C./mbar] |
|---|---|---|---|---|
| II-2 | H | H | 3-$CF_3$ | 65–69/0.05 |
| II-3 | Cl | H | H | 93–95/0.15 |
| II-4 | H | $C(CH_3)_3$ | H | 105–110/0.5⁻ |

Preparation of the precursors

Example (XV-1)

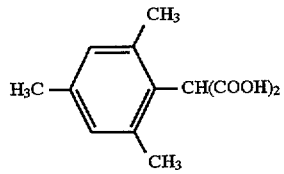

881 g (3.52 mol) of dimethyl mesitylmalonate and 690 g (12.32 mol) of potassium hydroxide are boiled for 12 hours in a mixture of 880 ml of water and 1,760 ml of methanol, and the mixture is cooled to room temperature and concentrated at a bath temperature of ≦30° C. The viscous residue is taken up in 2 l of water, the pH of the clear solution is brought to 1 using 1,060 ml of concentrated hydrochloric acid, and the mixture is cooled in an ice bath. The crystalline solid which has precipitated out is filtered off with suction, washed several times with cold water, and dried overnight in the air and subsequently over potassium hydroxide at 40° C. and 10 m-bar.

757 g (97% of theory) of mesitylmalonic acid of melting point 182°–184° C. (decomp.) are obtained, The precursors of the formula (XV)

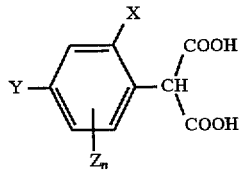

which are listed below in Table 3 are obtained analogously to Example (XV-1) taking into consideration the information in the description of the processes according to the invention:

| Ex. No. | | | | Physical constant |
|---|---|---|---|---|
| XV-2 | H | H | 3-CF$_3$ | M.p.: 123° C. (decomp.) |
| XV-3 | Cl | H | H | M.p.: 78–81° C. (decomp.) |
| XV-4 | H | C(CH$_3$)$_3$ | H | M.p.: 150–151° C. (decomp.) |

284 g (1.5 mol) of 2-fluoro-2-chloromethyl-1-bromopropane are added at room temperature to a mixture of 144 g (4.5 mol) of pure hydrazine and 1,000 ml of hydrazine hydrate, and the mixture is stirred for 3 hours at after cooling, the reaction mixture is extracted in a perforator for 18 hours, using diethyl ether. The ether solution is dried using potassium hydroxide pellets and concentrated. The residue is distilled at 10 mbar.

118 g (68% of theory) of 4-fluoro-4-methylpiperidazine (98% pure according to gas chromatography) are obtained.

Use Examples

In the Use Examples which follow, the compound listed below was employed as comparison substance:

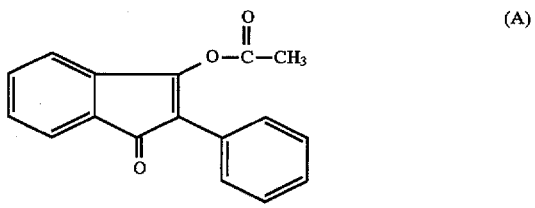

3-(Acetyloxy)-2-phenyl-1H-inden-1-one (disclosed in U.S. Pat. No. 4,104,043).

Example A
Tetranychus test (resistant)
Solvent:

7 parts by weight of dimethylformamide
Emulsifier:

1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Bean plants (*Phaseolus vulgaris*) which are heavily infested with all development stages of the greenhouse red spider mite or two-spotted spider mite (*Tetranychus urticae*) are treated by being dipped into the preparation of active compound of the desired concentration.

After the desired time, the destruction is determined in %. 100% means that all spider mites have been destroyed; 0% means that no spider mites have been destroyed.

In this test, a superior activity compared to the prior art is shown, for example, by the following compounds of the Preparation Examples: 1, 3, 4, 5 and 6.

Example B
Tetranychus test (OP-resistant)
Solvent:

7 parts by weight of dimethylformamide
Emulsifier:

1 part by weight of alkylaryl polyglycol ether

To produce a suitable preparation of active compound, 1 part by weight of active compound is mixed with the stated amount of solvent and the stated amount of emulsifier, and the concentrate is diluted with water containing emulsifier to the desired concentration.

Bean plants (*Phaseolus vulgaris*) which are heavily infested with all development stages of the greenhouse red spider mite or two-spotted spider mite (*Tetranychus urticae*) are sprayed with the preparation of active compound of the desired concentration until dripping wet.

After the desired time, the destruction is determined in %. 100% means that all spider mites have been destroyed; 0% means that no spider mites have been destroyed.

In this test, a superior activity compared to the prior art is shown, for example, by the following compounds of the Preparation Examples: 2, 8, 9, 10, 11 and 12.

Example C
Plutella test
Solvent:

7 parts by weight of dimethylformamide
Emulsifier:

1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of active compound of the desired concentration and infested with caterpillars of the cabbage moth (*Plutella maculipennis*) while the leaves are moist.

After the desired time, the destruction is determined in %. 100% means that all caterpillars have been destroyed; 0% means that no caterpillars have been destroyed.

In this test, a superior activity compared to the prior art is shown, for example, by the following compounds of the Preparation Examples: 2, 4, 5, 8, 9, 10 and 13.

Example D
Pre-emergence test
Solvent:

5 parts by weight of acetone
Emulsifier:

1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep the amount of water per unit area constant. The concentration of the active compound in the preparation is of no importance, only the amount of active compound applied per unit area being decisive. After three weeks, the degree of damage to the plants is rated in % damage in comparison with the development of the untreated control. The figures denote:

0%=no action (like untreated control)

100%=total destruction

In this test, a clearly superior activity and crop plant selectivity compared with the prior art is shown, for example, by the compounds of the following Preparation Examples: 1, 2, 3, 4, 5, 8, 9, 10 and 11.

Example E

Post-emergence test
Solvent:
5 parts by weight of acetone
Emulsifier:
1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of the active compound in such a way as to apply the particular amounts of active compound desired per unit area. The concentration of the spray liquor is chosen so that the particular amounts of active compound desired are applied in 1,000 l of water/ha. After three weeks, the degree of damage to the plants is rated in % damage in comparison with the development of the untreated control. The figures denote:

0%=no action (like untreated control)
100%=total destruction

In this test, a clearly superior activity and crop plant selectivity compared with the prior art is shown, for example, by the compounds of the following Preparation Examples: 1, 3, 4, 5, 8, 9, 10 and 11.

Example F

Test with resistant Lucilia cuprina larvae
Emulsifier:
35 parts by weight of ethylene glycol monomethyl ether
35 parts by weight of nonylphenyol polyglycol To produce a suitable preparation of active compound, three parts by weight of active compound are mixed with seven parts by weight of the abovementioned mixture, and the resulting concentrate is diluted with water to the particular desired concentration.

Approx. 20 resistant Lucilia cuprina larvae are introduced into a test tube which contains approx. 1 cm³ of horse meat and 0.5 ml of the preparation of active compound. The degree of destruction is determined after 24 hours.

In this test, the active compounds from Examples No. 1, 3, 4, 5, 7, 8, 9, 10, 11, 12, 13, 18, 19, 21, 22 and 24 showed a 100% destroying action at an active compound concentration of 1%.

We claim:

1. Halogenocarbonyl ketches of the formula (IIa)

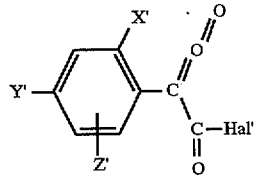

(IIa)

in which

Hal' stands for halogen

X' stands for $C_1$–$C_4$-alkyl, halogen or trifluoromethyl

Y' stands for hydrogen, $C_1$–$C_4$-alkyl, halogen or trifluoromethyl and

Z' stands for hydrogen, $C_1$–$C_4$-alkyl, halogen or trifluoromethyl with the proviso that Z' must not stand for hydrogen, if Y' stands for hydrogen.

2. Halogenocarbonyl ketenes of the formula (IIa) according to claim 1 in which

Hal' stands for bromine or chlorine.

X' stands for methyl, fluorine, chlorine, bromine or trifluoromethyl,

Y' stands for hydrogen, methyl, ethyl, n-propyl, i-propyl, n-butyl, i-butyl, tert-butyl, fluorine, chlorine, bromine or trifluoromethyl and Z' stands for hydrogen, methyl, fluorine, chlorine, bromine or trifluoromethyl with the proviso that Z' must not stand for hydrogen, if Y' stands for hydrogen.

3. Halogenocarbonyl ketenes of the formula (IIa) according to claim 1 in which

X', Y' and Z' either simultaneously stand for methyl or

X' and Y' stand for chlorine and Z' simultaneously means hydrogen.

4. Arylmalonic acids of the formula (XVIa)

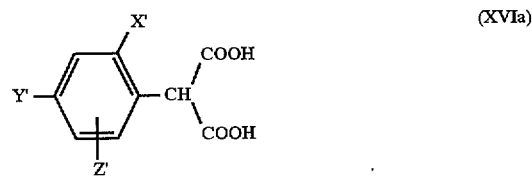

(XVIa)

in which

X' stands for $C_1$–$C_4$-alkyl, halogen or trifluoromethyl

Y' stands for hydrogen, $C_1$–$C_4$-alkyl, halogen or trifluoromethyl and

Z' stands for hydrogen, $C_1$–$C_4$-alkyl, halogen or trifluoromethyl with the proviso that Z' must not stand for hydrogen, if Y' stands for hydrogen.

* * * * *

UNITED STATES PATENT AND TRADEMARK OFFICE
CERTIFICATE OF CORRECTION

PATENT NO : 5,739,389
DATED : April 14, 1998
INVENTOR(S): Bernd-Wieland Kruger, et al.

It is certified that error appears in the above-identified patent and that said Letters Patent is hereby corrected as shown below:

| | |
|---|---|
| Title Page, "Inventors" Line 2 | Delete " Bergisch- Glabach " and substitute --- Bergisch-Gladbach --- |
| Title Page, "Other Publications" Line 6 | Delete " Heterocycleic " and substitute -- Heterocyclic -- |
| Col. 47, Claim 1, Line 1 | Delete " Ketches " and substitute -- Ketenes -- |
| Col. 47, Claim 1, Formula IIa | Delete " 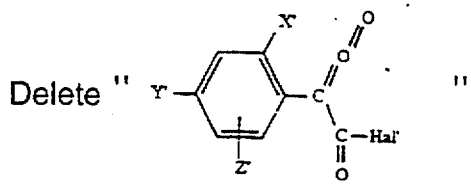 " |
| | and substitute with 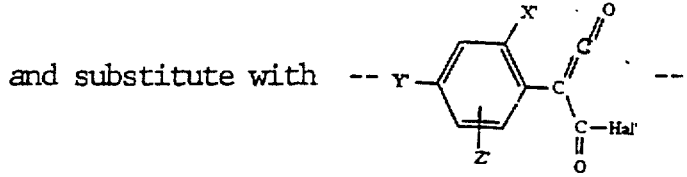 |

Signed and Sealed this

Sixteenth Day of November, 1999

Attest:

Q. TODD DICKINSON

*Attesting Officer*     *Acting Commissioner of Patents and Trademarks*